United States Patent
Sanghera et al.

(10) Patent No.: US 10,575,740 B2
(45) Date of Patent: Mar. 3, 2020

(54) SYSTEMS AND METHODS FOR SENSING VECTOR SELECTION IN AN IMPLANTABLE MEDICAL DEVICE

(71) Applicant: CAMERON HEALTH INC, St. Paul, MN (US)

(72) Inventors: Rick Sanghera, San Clemente, CA (US); Venugopal Allavatam, Maple Grove, MN (US)

(73) Assignee: CAMERON HEALTH INC., St. Paul, MN (US)

( * ) Notice: Subject to any disclaimer, the term of this patent is extended or adjusted under 35 U.S.C. 154(b) by 92 days.

(21) Appl. No.: 15/169,207

(22) Filed: May 31, 2016

(65) Prior Publication Data

US 2016/0270681 A1 Sep. 22, 2016

Related U.S. Application Data

(63) Continuation of application No. 14/304,084, filed on Jun. 13, 2014, now Pat. No. 9,364,677, which is a
(Continued)

(51) Int. Cl.
*A61B 5/04* (2006.01)
*A61B 5/0452* (2006.01)
(Continued)

(52) U.S. Cl.
CPC ...... *A61B 5/04011* (2013.01); *A61B 5/04012* (2013.01); *A61B 5/0422* (2013.01);
(Continued)

(58) Field of Classification Search
CPC .. A61B 5/04011; A61N 1/368; A61N 11/3918
See application file for complete search history.

(56) References Cited

U.S. PATENT DOCUMENTS

| 3,653,387 A | 4/1972 | Ceier |
| 3,710,374 A | 1/1973 | Kelly |

(Continued)

FOREIGN PATENT DOCUMENTS

| DE | 29801807 U1 | 6/1998 |
| EP | 0095727 A1 | 12/1983 |

(Continued)

OTHER PUBLICATIONS

"U.S. Appl. No. 11/120,284, Response filed Apr. 9, 2009 to NonFinal Office Action dated Jan. 12, 2009", 11 pages.
(Continued)

*Primary Examiner* — Carl H Layno
*Assistant Examiner* — Jennifer L Ghand
(74) *Attorney, Agent, or Firm* — Seager, Tufte & Wickhem LLP

(57) ABSTRACT

Methods and devices for sensing vector analysis in an implantable cardiac stimulus system. In an illustrative example, a first sensing vector is analyzed to determine whether it is suitable, within given threshold conditions, for use in cardiac event detection and analysis. If so, the first vector may be selected for detection and analysis. Otherwise, one or more additional vectors are analyzed. A detailed example illustrates methods for analyzing sensing vectors by the use of a scoring system. Devices adapted to perform these methods are also discussed, including implantable medical devices adapted to perform these methods, and systems comprising implantable medical devices and programmers adapted to communicate with implantable medical devices, the systems also being adapted to perform these methods. Another example includes a programmer configured to perform these methods including certain steps of directing operation of an associated implanted or implantable medical device.

20 Claims, 18 Drawing Sheets

Related U.S. Application Data continuation of application No. 11/441,522, filed on May 26, 2006, now Pat. No. 8,788,023.

(51) Int. Cl.
*A61N 1/37* (2006.01)
*A61N 1/372* (2006.01)
*A61N 1/39* (2006.01)
*A61N 1/368* (2006.01)
*A61B 5/042* (2006.01)
*A61B 5/00* (2006.01)

(52) U.S. Cl.
CPC ............ *A61B 5/0452* (2013.01); *A61B 5/686* (2013.01); *A61N 1/368* (2013.01); *A61N 1/3704* (2013.01); *A61N 1/37211* (2013.01); *A61N 1/3918* (2013.01); *A61N 1/3956* (2013.01); *A61B 5/0031* (2013.01)

(56) References Cited

U.S. PATENT DOCUMENTS

| | | |
|---|---|---|
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Wielders et al. |
| 4,550,502 A | 11/1985 | Grayzel |
| 4,567,900 A | 2/1986 | Moore |
| 4,589,420 A | 5/1986 | Adams et al. |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,779,617 A | 10/1988 | Whigham |
| 4,800,883 A | 1/1989 | Winstrom |
| 4,830,005 A | 5/1989 | Woskow |
| 4,944,300 A | 7/1990 | Saksena |
| 4,960,126 A | 10/1990 | Conlon et al. |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,137,025 A | 8/1992 | Turner, II |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,230,337 A | 7/1993 | Dahl et al. |
| 5,255,692 A | 10/1993 | Neubauer et al. |
| 5,261,400 A | 11/1993 | Bardy |
| 5,271,411 A | 12/1993 | Ripley et al. |
| 5,291,895 A | 3/1994 | McIntyre |
| 5,299,119 A | 3/1994 | Kraf et al. |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,370,667 A | 12/1994 | Alt |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,031 A | 5/1995 | Yomtov |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,693 A | 7/1995 | Schroeppel |
| 5,439,485 A | 8/1995 | Mar et al. |
| 5,441,518 A | 8/1995 | Adams et al. |
| 5,447,521 A | 9/1995 | Anderson et al. |
| 5,464,431 A | 11/1995 | Adams et al. |
| 5,476,503 A | 12/1995 | Yang |
| 5,501,702 A | 3/1996 | Plicchi et al. |
| 5,509,923 A | 4/1996 | Middleman et al. |
| 5,509,928 A | 4/1996 | Acken |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,540,727 A | 7/1996 | Tockman et al. |
| 5,558,098 A | 9/1996 | Fain |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,755,738 A | 5/1998 | Kim et al. |
| 5,766,226 A | 6/1998 | Pedersen |
| 5,776,169 A | 7/1998 | Schroeppel |
| 5,814,090 A | 9/1998 | Latterell et al. |
| 5,827,326 A | 10/1998 | Kroll et al. |
| 5,836,976 A | 11/1998 | Min et al. |
| 5,843,132 A | 12/1998 | Ilvento |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,987,352 A | 11/1999 | Klein et al. |
| 5,999,853 A | 12/1999 | Stoop et al. |
| 6,014,586 A | 1/2000 | Weinberg et al. |
| 6,016,442 A | 1/2000 | Hsu et al. |
| 6,026,325 A | 2/2000 | Weinberg et al. |
| 6,029,086 A | 2/2000 | Kim et al. |
| 6,044,297 A | 3/2000 | Sheldon et al. |
| 6,058,328 A | 5/2000 | Levine et al. |
| 6,093,173 A | 7/2000 | Balceta et al. |
| 6,095,987 A | 8/2000 | Shmulewitz et al. |
| 6,115,628 A | 9/2000 | Stadler et al. |
| H001905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |

(56) References Cited

U.S. PATENT DOCUMENTS

| | | | |
|---|---|---|---|
| 6,185,450 B1 | 2/2001 | Seguine et al. |
| 6,190,324 B1 | 2/2001 | Kieval et al. |
| 6,236,882 B1 | 5/2001 | Lee et al. |
| 6,266,554 B1 | 7/2001 | Hsu et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,308,095 B1 | 10/2001 | Hsu et al. |
| 6,334,071 B1 | 12/2001 | Lu |
| 6,345,198 B1 | 2/2002 | Mouchawar et al. |
| 6,377,844 B1 | 4/2002 | Graen |
| 6,381,493 B1 | 4/2002 | Stadler et al. |
| 6,411,844 B1 | 6/2002 | Kroll et al. |
| 6,490,486 B1 | 12/2002 | Bradley |
| 6,493,579 B1 | 12/2002 | Gilkerson et al. |
| 6,493,584 B1 | 12/2002 | Lu |
| 6,496,715 B1 | 12/2002 | Lee et al. |
| 6,516,225 B1 | 2/2003 | Florio |
| 6,539,257 B1 | 3/2003 | KenKnight |
| 6,567,691 B1 | 5/2003 | Stadler |
| 6,574,505 B1 | 6/2003 | Warren |
| 6,587,720 B2 | 7/2003 | Hsu et al. |
| 6,625,490 B1 | 9/2003 | McClure et al. |
| 6,636,762 B2 | 10/2003 | Begemann |
| 6,647,292 B1 | 11/2003 | Bardy et al. |
| 6,658,292 B2 | 12/2003 | Kroll et al. |
| 6,658,293 B2 | 12/2003 | Vonk |
| 6,684,100 B1 | 1/2004 | Sweeney et al. |
| 6,687,540 B2 | 2/2004 | Marcovecchio |
| 6,699,200 B2 | 3/2004 | Cao et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,728,575 B2 | 4/2004 | Hedberg |
| 6,731,978 B2 | 5/2004 | Olson et al. |
| 6,738,667 B2 | 5/2004 | Deno et al. |
| 6,745,076 B2 | 6/2004 | Wohlgemuth et al. |
| 6,751,502 B2 | 6/2004 | Daum et al. |
| 6,754,528 B2 | 6/2004 | Bardy et al. |
| 6,760,615 B2 | 7/2004 | Ferek-Petric |
| 6,766,190 B2 | 7/2004 | Ferek-Petric |
| 6,778,860 B2 | 8/2004 | Ostroff et al. |
| 6,788,974 B2 | 9/2004 | Bardy et al. |
| 6,810,284 B1 | 10/2004 | Bradley |
| 6,834,204 B2 | 12/2004 | Ostroff et al. |
| 6,892,092 B2 | 5/2005 | Palreddy et al. |
| 6,909,916 B2 | 6/2005 | Spinelli et al. |
| 6,959,212 B2 | 10/2005 | Hsu et al. |
| 6,980,856 B2 | 12/2005 | Sullivan et al. |
| 6,993,379 B1 | 1/2006 | Kroll et al. |
| 6,996,434 B2 | 2/2006 | Marcovecchio et al. |
| 7,016,730 B2 | 3/2006 | Ternes |
| 7,020,523 B1 | 3/2006 | Lu et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,039,463 B2 | 5/2006 | Marcovecchio |
| 7,130,689 B1 | 10/2006 | Turcott |
| 7,167,747 B2 | 1/2007 | Gunderson et al. |
| 7,181,281 B1 | 2/2007 | Kroll |
| 7,266,409 B2 | 9/2007 | Gunderson |
| 7,366,569 B2 | 4/2008 | Belalcazar |
| 7,392,085 B2 | 6/2008 | Warren et al. |
| 7,412,287 B2 | 8/2008 | Yonce et al. |
| 7,627,367 B2 | 12/2009 | Warren et al. |
| 7,783,340 B2 | 8/2010 | Sanghera et al. |
| 8,200,341 B2 | 6/2012 | Sanghera et al. |
| 8,483,843 B2 | 7/2013 | Sanghera et al. |
| 8,788,023 B2 | 7/2014 | Sanghera et al. |
| 2001/0027330 A1 | 10/2001 | Sullivan et al. |
| 2001/0034487 A1 | 10/2001 | Cao et al. |
| 2002/0165587 A1 | 11/2002 | Zhang et al. |
| 2002/0169484 A1 | 11/2002 | Mathis et al. |
| 2003/0083710 A1 | 5/2003 | Ternes et al. |
| 2003/0144700 A1 | 7/2003 | Brown et al. |
| 2003/0191500 A1 | 10/2003 | Stokes et al. |
| 2003/0204215 A1 | 10/2003 | Gunderson et al. |
| 2004/0049120 A1* | 3/2004 | Cao ............... A61B 5/0456 600/521 |
| 2004/0088018 A1 | 5/2004 | Sawchuk et al. |
| 2004/0215240 A1 | 10/2004 | Lovett et al. |
| 2004/0230229 A1 | 11/2004 | Lovett et al. |
| 2004/0230243 A1 | 11/2004 | Haefner et al. |
| 2004/0230249 A1 | 11/2004 | Haefner |
| 2004/0236379 A1 | 11/2004 | Bardy et al. |
| 2004/0254611 A1 | 12/2004 | Palreddy et al. |
| 2004/0254613 A1 | 12/2004 | Ostroff et al. |
| 2005/0004615 A1 | 1/2005 | Sanders |
| 2005/0049644 A1* | 3/2005 | Warren ............ A61B 5/0402 607/9 |
| 2005/0203581 A1 | 9/2005 | Spinelli et al. |
| 2005/0245976 A1 | 11/2005 | Wang |
| 2006/0036288 A1 | 2/2006 | Bocek et al. |
| 2006/0052830 A1 | 3/2006 | Spinelli et al. |
| 2006/0079796 A1 | 4/2006 | Marcovecchio et al. |
| 2006/0085038 A1 | 4/2006 | Linder et al. |
| 2006/0116730 A1 | 6/2006 | Gunderson |
| 2006/0161205 A1 | 7/2006 | Mitrani et al. |
| 2006/0167502 A1 | 7/2006 | Haefner |
| 2006/0173498 A1 | 8/2006 | Banville et al. |
| 2006/0235476 A1 | 10/2006 | Gunderson et al. |
| 2006/0241512 A1 | 10/2006 | Kwok et al. |
| 2007/0123947 A1 | 5/2007 | Wenger et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233196 A1 | 10/2007 | Stadler et al. |
| 2007/0233198 A1 | 10/2007 | Ghanem et al. |
| 2007/0239044 A1 | 10/2007 | Ghanem et al. |
| 2007/0239045 A1 | 10/2007 | Ghanem et al. |
| 2007/0239046 A1 | 10/2007 | Ghanem et al. |
| 2007/0239047 A1 | 10/2007 | Ghanem et al. |
| 2007/0239048 A1 | 10/2007 | Ghanem et al. |
| 2007/0239049 A1 | 10/2007 | Ghanem et al. |
| 2007/0239050 A1 | 10/2007 | Ghanem et al. |
| 2007/0239051 A1 | 10/2007 | Ghanem et al. |
| 2007/0239220 A1 | 10/2007 | Greenhut et al. |
| 2007/0270704 A1 | 11/2007 | Ghanem et al. |
| 2007/0276445 A1 | 11/2007 | Sanghera et al. |
| 2007/0276452 A1 | 11/2007 | Sanghera et al. |
| 2008/0188901 A1 | 8/2008 | Sanghera et al. |
| 2008/0243025 A1 | 10/2008 | Holmstrom et al. |
| 2008/0269813 A1 | 10/2008 | Greenhut et al. |
| 2009/0093731 A1 | 4/2009 | Palreddy et al. |
| 2012/0245651 A1 | 9/2012 | Sanghera et al. |
| 2013/0274822 A1 | 10/2013 | Sanghera et al. |

FOREIGN PATENT DOCUMENTS

| | | |
|---|---|---|
| EP | 0316616 A2 | 5/1989 |
| EP | 0347353 A1 | 12/1989 |
| EP | 0316616 A3 | 6/1992 |
| EP | 0517494 A2 | 12/1992 |
| EP | 0518599 A2 | 12/1992 |
| EP | 0517494 A3 | 3/1993 |
| EP | 0536873 A1 | 4/1993 |
| EP | 0586858 A1 | 3/1994 |
| EP | 0627237 A1 | 12/1994 |
| EP | 0641573 A2 | 3/1995 |
| EP | 0677301 A1 | 10/1995 |
| EP | 0641573 A3 | 6/1997 |
| EP | 0518599 B1 | 9/1997 |
| EP | 0813889 A2 | 12/1997 |
| EP | 0917887 A1 | 5/1999 |
| EP | 0923130 A1 | 6/1999 |
| EP | 1000634 A1 | 5/2000 |
| EP | 1745741 A1 | 1/2007 |
| WO | 9319809 A1 | 10/1993 |
| WO | 9729802 A2 | 8/1997 |
| WO | 9825349 A1 | 6/1998 |
| WO | 9903534 A1 | 1/1999 |
| WO | 9937362 A1 | 7/1999 |
| WO | 9948554 A1 | 9/1999 |
| WO | 9953991 A1 | 10/1999 |

(56) References Cited

FOREIGN PATENT DOCUMENTS

| | | |
|---|---|---|
| WO | 0041766 A1 | 7/2000 |
| WO | 0050120 A1 | 8/2000 |
| WO | 0143649 A1 | 6/2001 |
| WO | 0156166 A2 | 8/2001 |
| WO | 022208 A3 | 3/2002 |
| WO | 0222208 A2 | 3/2002 |
| WO | 0224275 A2 | 3/2002 |
| WO | 0224275 A3 | 5/2002 |
| WO | 02068046 A1 | 9/2002 |
| WO | 03018121 A2 | 3/2003 |
| WO | 03020367 A1 | 3/2003 |
| WO | 03065613 A1 | 8/2003 |
| WO | 2004091720 A2 | 10/2004 |
| WO | 2004105871 A1 | 12/2004 |
| WO | 2004108212 A2 | 12/2004 |
| WO | 2007089959 A1 | 8/2007 |
| WO | 2007140207 A1 | 12/2007 |
| WO | 2007140209 A2 | 12/2007 |
| WO | 2007140214 A1 | 12/2007 |
| WO | 2007140209 A3 | 4/2008 |

OTHER PUBLICATIONS

"U.S. Appl. No. 11/441,516, Final Office Action dated Apr. 8, 2009", 19 pages.
"U.S. Appl. No. 11/441,516, NonFinal Office Action dated Nov. 25, 2008", 18 pages.
"U.S. Appl. No. 11/441,516, Response filed Feb. 25, 2009 to NonFinal Office Action dated Nov. 25, 2009", 25 pages.
"U.S. Appl. No. 11/441,522, Advisory Action dated May 26, 2011", 3 pages.
"U.S. Appl. No. 11/441,522, Advisory Action dated Jul. 13, 2010", 3 pages.
"U.S. Appl. No. 11/441,522, Advisory Action dated Sep. 4, 2009", 3 pages.
"U.S. Appl. No. 11/441,522, Final Office Action dated Mar. 7, 2011", 21 pages.
"U.S. Appl. No. 11/441,522, Final Office Action dated Apr. 29, 2010", 6 pages.
"U.S. Appl. No. 11/441,522, Final Office Action dated Jun. 22, 2009", 17 pages.
"U.S. Appl. No. 11/441,522, NonFinal Office Action dated Dec. 23, 2008", 18 pages.
"U.S. Appl. No. 11/441,522, NonFinal Office Action dated Sep. 16, 2010", 23 pages.
"U.S. Appl. No. 11/441,522, NonFinal Office Action dated Oct. 2, 2013", 6 pages.
"U.S. Appl. No. 11/441,522, NonFinal Office Action dated Oct. 27, 2009", 17 pages.
"U.S. Appl. No. 11/441,522, Notice of Allowance dated Mar. 11, 2014", 8 pages.
"U.S. Appl. No. 11/441,522, Preliminary Amendment filed Nov. 26, 2008", 10 pages.
"U.S. Appl. No. 11/441,522, Response filed Jan. 27, 2010 to NonFinal Office Action dated Oct. 27, 2009", 13 pages.
"U.S. Appl. No. 11/441,522, Response filed Mar. 23, 2009 to NonFinal Office Action dated Dec. 23, 2008", 12 pages.
"U.S. Appl. No. 11/441,522, Response filed May 6, 2011 to Final Office Action dated Mar. 7, 2011", 14 pages.
"U.S. Appl. No. 11/441,522, Response filed Jun. 6, 2011 to Final Office Action dated Mar. 7, 2011", 14 pages.
"U.S. Appl. No. 11/441,522, Response filed Jun. 29, 2010 to Final Office Action dated Apr. 29, 2010", 12 pages.
"U.S. Appl. No. 11/441,522, Response filed Aug. 24, 2009 to Final Office Action dated Jun. 22, 2009", 11 pages.
"U.S. Appl. No. 11/441,522, Response filed Aug. 27, 2010 to Final Office Action dated Apr. 29, 2010", 14 pages.
"U.S. Appl. No. 11/441,522, Response filed Sep. 22, 2009 to Advisory Action dated Sep. 4, 2009", 13 pages.
"U.S. Appl. No. 11/441,522, Response filed Dec. 3, 2013 to NonFinal Office Action dated Oct. 2, 2013", 14 pages.
"U.S. Appl. No. 11/441,522, Response filed Dec. 16, 2010 to NonFinal Office Action dated Sep. 16, 2010", 18 pages.
"U.S. Appl. No. 11/442,228, Advisory Action dated Jul. 12, 2013", 3 pages.
"U.S. Appl. No. 11/442,228, Advisory Action dated Dec. 1, 2010", 3 pages.
"U.S. Appl. No. 11/442,228, Advisory Action dated Dec. 22, 2009", 3 pages.
"U.S. Appl. No. 11/442,228, Decision on Pre-Appeal Brief Request dated Mar. 11, 2010", 2 pages.
"U.S. Appl. No. 11/442,228, Final Office Action dated Apr. 29, 2013", 9 pages.
"U.S. Appl. No. 11/442,228, Final Office Action dated Jul. 10, 2009", 8 pages.
"U.S. Appl. No. 11/442,228, Final Office Action dated Sep. 15, 2010", 9 pages.
"U.S. Appl. No. 11/442,228, Final Office Action dated Oct. 2, 2009", 8 pages.
"U.S. Appl. No. 11/442,228, NonFinal Office Action dated Jan. 16, 2013", 10 pages.
"U.S. Appl. No. 11/442,228, NonFinal Office Action dated Apr. 14, 2010", 4 pages.
"U.S. Appl. No. 11/442,228, NonFinal Office Action dated Dec. 23, 2008", 19 pages.
"U.S. Appl. No. 11/442,228, Pre-Appeal Brief Request filed Jan. 4, 2010", 4 pages.
"U.S. Appl. No. 11/442,228, Response filed Mar. 20, 2013 to NonFinal Office Action dated Jan. 16, 2013", 8 pages.
"U.S. Appl. No. 11/442,228, Response filed Apr. 23, 2009 to NonFinal Office Action dated Aug. 23, 2008", 7 pages.
"U.S. Appl. No. 11/442,228, Response filed Jul. 1, 2013 to Final Office Action dated Apr. 29, 2013", 12 pages.
"U.S. Appl. No. 11/442,228, Response filed Jul. 14, 2010 to NonFinal Office Action dated Apr. 14, 2010", 8 pages.
"U.S. Appl. No. 11/442,228, Response filed Sep. 10, 2009 to Final Office Action dated Jul. 10, 2009", 8 pages.
"U.S. Appl. No. 11/442,228, Response filed Nov. 12, 2010 to Final Office Action dated Sep. 15, 2010", 7 pages.
"U.S. Appl. No. 11/442,228, Response filed Dec. 2, 2009 to Final Office Action dated Oct. 2, 2009", 7 pages.
"U.S. Appl. No. 11/442,228, Response filed Dec. 15, 2010 to Advisory Action dated Dec. 1, 2010", 7 pages.
"U.S. Appl. No. 11/623,472, NonFinal Office Action dated Aug. 20, 2009", 14 pages.
"U.S. Appl. No. 11/623,472, Response filed Nov. 20, 2009 to NonFinal Office Action dated Aug. 20, 2009", 15 pages.
"U.S. Appl. No. 11/672,353, Final Office Action dated Aug. 19, 2009", 11 pages.
"U.S. Appl. No. 11/672,353, NonFinal Office Action dated Feb. 24, 2009", 15 pages.
Throne et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, pp. 561-570, Jun. 1991.
Tietze et al., "Halbleiter-Schaltungstechnik", © Springer-Verlag (Berlin, Germany), pp. 784-786, 1991.
Valenzuela et al., "Outcomes of Rapid Defibrillation by Security Officers After Cardiac Arrest in Casinos", The New England Journal of Medicine, vol. 343, No. 17, pp. 1206-1209, Oct. 26, 2000.
Walters et al., "Analog to Digital Conversion Techniques in Implantable Devices", Annual International Conference of the IEEE Engineering in Medicine and Biology Society, vol. 13, No. 4, pp. 1674-1676, 1991.
"U.S. Appl. No. 11/672,353, Response filed May 26, 2009 to NonFinal Office Action dated Feb. 24, 2009", 12 pages.
"U.S. Appl. No. 11/672,353, Response filed Dec. 17, 2009 to Final Office Action dated Aug. 19, 2009", 9 pages.
"U.S. Appl. No. 13/491,529, NonFinal Office Action dated Nov. 19, 2012", 7 pages.

(56) References Cited

OTHER PUBLICATIONS

"U.S. Appl. No. 13/491,529, Response filed Feb. 13, 2013 to NonFinal Office Action dated Nov. 19, 2012", 10 pages.
"U.S. Appl. No. 13/491,529, Response filed Oct. 17, 2012 to Restriction Requirement dated Sep. 17, 2012", 7 pages.
"U.S. Appl. No. 13/919,147, NonFinal Office Action dated Nov. 7, 2013", 5 pages.
"U.S. Appl. No. 13/919,147, Preliminary Amendment filed Jun. 18, 2013", 5 pages.
"U.S. Appl. No. 60/186,235, filed Mar. 1, 2000", 17 pages.
U.S. Appl. No. 60/632,000, filed Dec. 1, 2004, 30 pages.
"U.S. Appl. No. 60/786,981, filed Mar. 29, 2006", 71 pages.
"Australian Application Serial No. 2008213812, Examiner Report dated Apr. 17, 2012", 2 pages.
"Australian Application Serial No. 2008213812, Examiner Response filed Sep. 28, 2012 to Examiner Report dated Apr. 17, 2012", 63 pages.
"European Application Serial No. 07762301.5, Office Action dated Jan. 16, 2009", 2 pages.
"European Application Serial No. 07762301.5, Office Action dated Jun. 30, 2010", 4 pages.
"European Application Serial No. 07762301.5, Response filed Dec. 14, 2010 to Office Action dated Jun. 30, 2010", 8 pages.
"European Application Serial No. 07784075.9, Examination Notification Art. 94(3) dated Jun. 20, 2011", 6 pages.
"European Application Serial No. 07784075.9, Office Action dated Jan. 16, 2009", 2 pages.
"European Application Serial No. 07784075.9, Response filed Oct. 28, 2011 to Examination Notification Art. 94(3) dated Jun. 20, 2011", 7 pages.
"European Application Serial No. 08729181.1, Examination Notification Art. 94(3) dated Mar. 16, 2010", 4 pages.
"European Application Serial No. 08729181.1, Examination Notification Art. 94(3) dated Nov. 28, 2012", 4 pages.
"European Application Serial No. 08729181.1, Response filed Apr. 8, 2013 to Examination Notification Art. 94(3) dated Nov. 28, 2012", 9 pages.
"European Application Serial No. 08729181.1, Response filed Jul. 28, 2010 to Examination Notification Art. 94(3) dated Mar. 16, 2010", 11 pages.
"International Application Serial No. PCT/US2007/069540, International Preliminary Report on Patentability dated Aug. 26, 2009", 8 pages.
"International Application Serial No. PCT/US2007/069540, International Search Report dated Oct. 25, 2007", 3 pages.
"International Application Serial No. PCT/US2007/069540, Written Opinion dated Oct. 25, 2007", 6 pages.
"International Application Serial No. PCT/US2007/069554, International Preliminary Report on Patentability dated Aug. 25, 2009", 8 pages.
"International Application Serial No. PCT/US2007/069554, International Search Report dated Oct. 22, 2007", 3 pages.
"International Application Serial No. PCT/US2007/069554, Written Opinion dated Oct. 22, 2007", 6 pages.
"International Application Serial No. PCT/US2008/053197, International Preliminary Report on Patentability dated Aug. 11, 2009", 9 pages.
"International Application Serial No. PCT/US2008/053197, International Search Report dated Jun. 25, 2008", 4 pages.
"International Application Serial No. PCT/US2008/053197, Written Opinion dated Jun. 25, 2008", 8 pages.
Bardy et al., "Multicenter Experience with a Pectoral Unipolar Implantable Cardioverter-Defibrillator", JACC, vol. 28, No. 2, pp. 400-410, Aug. 1996.
Burri et al., "Utility of the Surface ECG Before VDD Pacemaker Implantation", International Journal of Cardiology, vol. 117, No. 2, pp. 211-213, Apr. 25, 2007.
Cao et al., "An Implantable Medical Device with Multi-Vector Sensing Electrodes", U.S. Appl. No. 60/186,235, filed Mar. 1, 2000, 4 pages.
Chrysostomakis et al., "Implantable Loop Recorder Undersensing Mimicking Complete Heart Block", Europace, vol. 4, No. 2, pp. 211-213, 2002.
Chrysostomakis et al., "Sensing Issues Related to the Clinical Use of Implantable Loop Recorders", Europace, vol. 5, No. 2, pp. 143-148, 2003.
Friedman et al., "Implantable Defibrillators in Children: From Whence to Shock", Journal of Cardiovascular Electrophysiology, vol. 12, No. 3, pp. 361-362, Mar. 2001.
Ge et al., "Cardiac Arrhythmia Classification Using Autoregressive Modeling", Biomedical Engineering OnLine, [Online], retrieved from the Internet: <http://www.biomedical-engineering-online.com>, 12 pages, Nov. 13, 2002.
Gradaus et al., "Nonthoracotomy Implantable Cardioverter Defibrillator Placement in Children: Use of Subcutaneous Array Leads and Abdominally Placed Implantable Cardioverter Defibrillators in Children", Journal of Cardiovascular Electrophysiology, 12(3), pp. 356-360, Mar. 2001.
Gunderson, "Identification of Oversensing in a Medical Device", U.S. Appl. No. 60/632,000, filed Dec. 1, 2004, 30 pages.
Higgins et al., "The First Year Experience with the Dual Chamber ICD", Pace, vol. 23, pp. 18-25, Jan. 2000.
Mirowski et al., "Automatic Detection and Defibrillation of Lethal Arrhythmias—A New Concept", JAMA, vol. 213, No. 4, pp. 615-616, Jul. 27, 1970.
Olson et al., "Onset and Stability for Ventricular Tachyarrhythmia Detection in an Implantable Pacer-Cardioverter-Defibrillator", IEEE, pp. 167-170, 1987.
Schuder, "Completely Implanted Defibrillator", JAMA, vol. 214, No. 6, p. 1123, Nov. 9, 1970.
Schuder et al., "Experimental Ventricular Defibrillation with an Automatic and Completely Implanted System", Trans. Am. Soc. Artif. Int. Organs, vol. 16, pp. 207-212, 1970.
Schuder et al., "Standby Implanted Defibrillators", Arch. Intern. Med., vol. 127, p. 317, Feb. 1971.
Schuder, "The Role of an Engineering Oriented Medical Research Group in Developing Improved Methods & Devices for Achieving Ventricular Defibrillation: The University of Missouri Experience", PACE, vol. 16, Part 1, pp. 95-124, Jan. 1993.
Schuder et al., "Transthoracic Ventricular Defibrillation in the Dog with Truncated and Untruncated Exponential Stimuli", IEEE Trans. On Bio-Medical Engin., vol. BMD-18, No. 6, pp. 410-415, Nov. 1971.
Schwake et al., "Komplikationem mit Sonden bei 340 Patienten mit einem Implantierbaren Kardioverter/Defibrilator", Z. Kardiol, vol. 88, No. 8, pp. 559-565, 1999.
Stadler et al., "Method and Apparatus for Detecting Arrhythmias in a Subcutaneous Device", U.S. Appl. No. 50/786,981, filed Mar. 29, 2006, 71 pages.

* cited by examiner

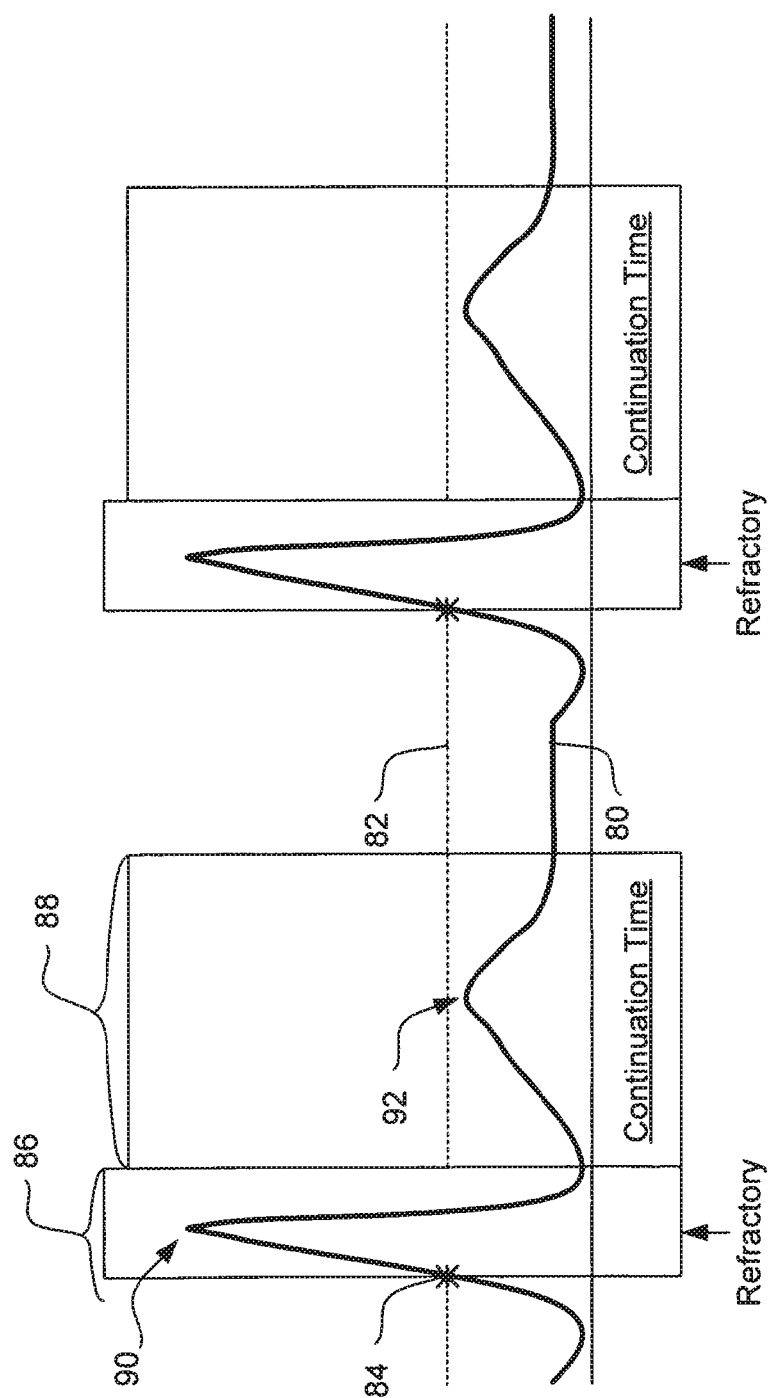

ically, the present invention
SYSTEMS AND METHODS FOR SENSING VECTOR SELECTION IN AN IMPLANTABLE MEDICAL DEVICE

RELATED APPLICATIONS

This application is a continuation of U.S. application Ser. No. 14/304,084, filed Jun. 13, 2014, now U.S. Pat. No. 9,364,677, which is a continuation of U.S. application Ser. No. 11/441,522, filed May 26, 2006, now U.S. Pat. No. 8,788,023. This application is related to U.S. application Ser. No. 11/441,516 filed on May 26, 2006, now issued as U.S. Pat. No. 7,623,909, and is titled IMPLANTABLE MEDICAL DEVICES AND PROGRAMMERS ADAPTED FOR SENSING VECTOR SELECTION, and is related to U.S. application Ser. No. 11/442,228, filed on May 26, 2006 and titled IMPLANTABLE MEDICAL DEVICE SYSTEMS HAVING INITIALIZATION FUNCTIONS AND METHODS OF OPERATION.

FIELD

The present invention relates to the field of implantable medical devices. More specifically, the present invention relates to implantable medical devices that detect cardiac activity.

BACKGROUND

Implantable cardiac stimulus devices often include circuitry for detection of electrical cardiac activity to observe a patient's cardiac function. Methods of and devices adapted for identifying and/or selecting favorable sensing vectors are desired.

SUMMARY

The present invention, in a first illustrative embodiment, includes a method of analyzing available sensing vectors to select a suitable sensing vector for use in cardiac event detection. The illustrative method attempts to select a sensing vector without a need for operator input by analyzing one or more sensing vectors to determine if a suitable sensing vector is available. If the analysis is inconclusive, the method may include requesting input from an operator to resolve apparent ambiguities in one or more sensed signals. Another illustrative embodiment includes an implantable cardiac stimulus device adapted to perform the method of, or methods similar to, the first illustrative embodiment. Yet another illustrative embodiment includes an external programmer for use with an implantable cardiac stimulus device, wherein the external programmer is adapted to perform the method of, or methods similar to, the first illustrative embodiment.

An illustrative embodiment also includes a method of sensing vector analysis in an implantable cardiac stimulus device that includes observing whether a first vector is suitable, within a given set of threshold conditions, for cardiac event detection and, if so, selecting the first vector for use in detection without considering additional vectors. If not, one or more additional vectors may be analyzed as well. If none of the analyzed sensing vectors meet the threshold conditions, the best available vector may be selected.

Another illustrative embodiment includes a detailed method of analyzing a sensing vector. The detailed illustrative method may include characterizing detected events as QRS events, artifacts, or unidentifiable. If sufficient detected events are characterized as QRS events, the sensing vector used to capture the detected events may be assessed for the quality of signal it receives. Otherwise, additional analysis of the unidentifiable events may seek to further categorize these events to allow assessment of the quality of signal captured by the sensing vector.

Yet another illustrative embodiment includes a method of cardiac signal analysis in an implantable cardiac stimulus system having a plurality of sensing electrodes and operational circuitry coupled thereto. The illustrative method is performed by operational circuitry executing vectoring instructions relative to a first sensing vector. In the illustrative method, the vectoring instructions cause the operational circuitry to return one of: a score indicating the quality of a signal captured along the first sensing vector; at least two possible scores indicating the quality of the signal captured along the first sensing vector wherein operator input is needed to determine which possible score is correct; or an indication that the sensing vector under review is unsuitable for cardiac signal sensing. The operational circuitry then determines whether the first sensing vector receives a score indicating that the first sensing vector is well suited to cardiac signal detection, and if not, the operational circuitry executes the vectoring instructions relative to a second sensing vector. Devices adapted for these methods make up additional illustrative embodiments.

Another illustrative embodiment includes a method of cardiac signal analysis in a programmer adapted for use in conjunction with an implantable cardiac stimulus device. The programmer may include operational circuitry for executing vectoring instructions relative to a first sensing vector. In the illustrative method, the vectoring instructions cause the operational circuitry to return one of: a score indicating the quality of a signal captured along the first sensing vector; at least two possible scores indicating the quality of the signal captured along the first sensing vector wherein operator input is needed to determine which possible score is correct; or an indication that the sensing vector under review is unsuitable for cardiac signal sensing. The programmer operational circuitry then determines whether the first sensing vector receives a score indicating that the first sensing vector is well suited to cardiac signal detection, and if not, the programmer operational circuitry executes the vectoring instructions relative to a second sensing vector. Devices adapted for these methods make up additional illustrative embodiments.

Yet further illustrative embodiments make use of sensing vector selection methods as described above, with first and second sensing vectors being identified as primary and secondary detection vectors or analysis vectors. Devices, including at least implantable cardiac stimulus devices and/or programmers for use with implantable cardiac stimulus devices which are adapted for such methods, make up additional illustrative embodiments.

BRIEF DESCRIPTION OF THE DRAWINGS

FIGS. 3A-3B are graphical representations of cardiac signals illustrating an analytical form for identifying QRS and T-Waves;

DETAILED DESCRIPTION

The following detailed description should be read with reference to the drawings. The drawings, which are not necessarily to scale, depict illustrative embodiments and are not intended to limit the scope of the invention.

Figure 1A:
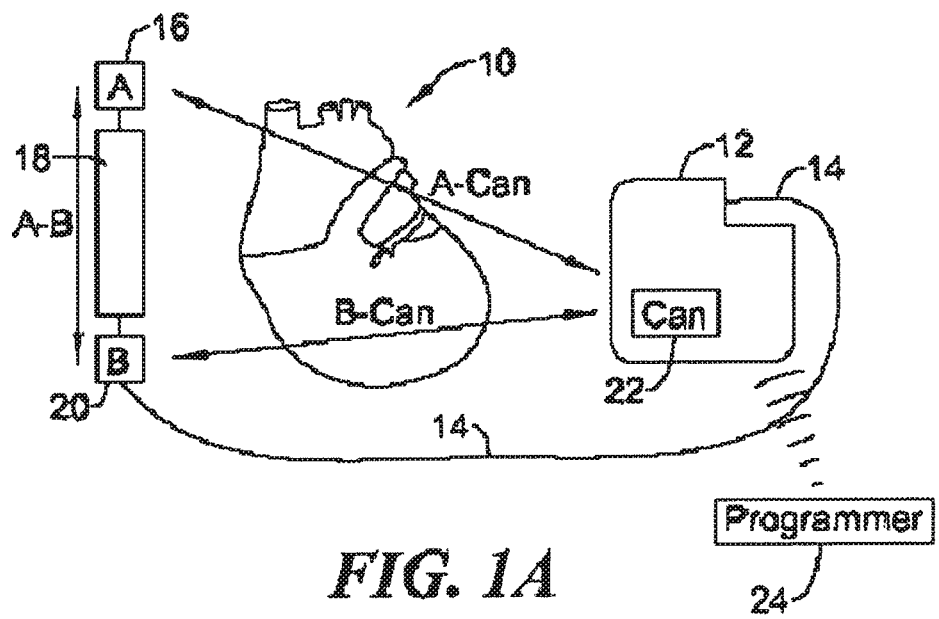
FIGS. 1A-1B, respectively, show subcutaneous and transvenous implanted cardiac stimulus systems relative to the heart.
Figure 1B:
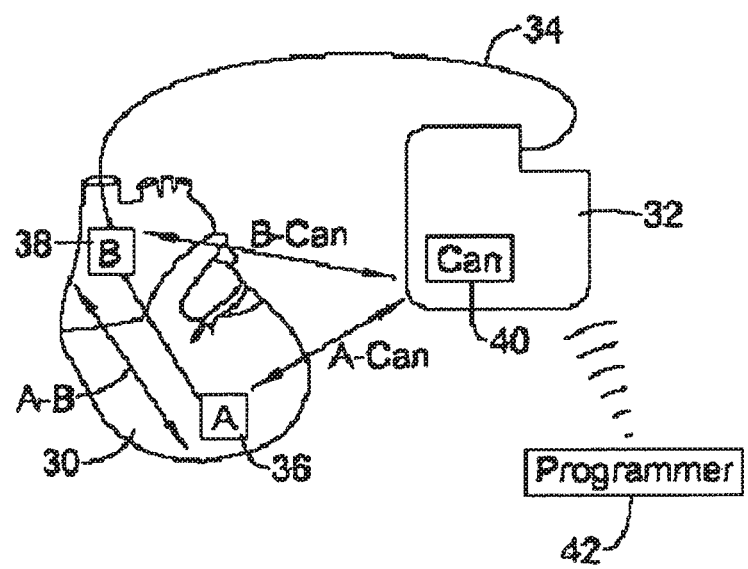

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister and includes sensing electrode A 16, coil electrode 18, and sensing electrode B 20. A can electrode 22 is shown on the canister 12. Several vectors for sensing are therefore available including A-can, B-can, and A-B. It should be noted that the use of the coil electrode 18 as a sensing electrode is also possible. Illustrative subcutaneous systems are shown in U.S. Pat. Nos. 6,647,292 and 6,721,597, and the disclosures of these patents are incorporated herein by reference. Some embodiments include a unitary system having two or more electrodes on a housing as set forth in the '292 patent, rather than that which is shown. A unitary system including an additional lead may also be used.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included, and also may be used for sensing in some embodiments of the present invention. In the illustrative example, electrode A 36 is located generally in the patient's ventricle, and electrode B 38 is located generally in the patient's atrium. The lead 34 may be anchored into the patient's myocardium. Again, a can electrode 40 is shown on the canister 32. With this system, plural sensing vectors may be defined as well. In both FIGS. 1A and 1B, one or more sensing electrodes may also be used for stimulus delivery. Some embodiments of the present invention may be used in combination systems that may include sensing vectors defined between two subcutaneous electrodes, a subcutaneous electrode and a transvenous electrode, and two transvenous electrodes.

In the configurations of FIGS. 1A and 1B, there are multiple sensing vectors available. Detection of cardiac function along one of these sensing vectors allows the implanted cardiac stimulus system to determine whether treatment is indicated due to the detection and identification of a malignant condition such as, for example, a ventricular tachycardia. An implanting physician may perform vector selection by directly diagnosing which of the captured vectors is best. However, this requires an assessment of cardiac function along several vectors and may increase the time needed to perform implantation, and also increases the risk of human error. Further, if the physician is needed to perform vector selection, as patient physiology changes (which may happen if a fibroid develops around an implanted sensing electrode), the system is at risk of using a sub-optimal sensing vector until the patient re-visits the physician. Finally, the selection of a vector has often been a task requiring specialized training, as selection of a suitable vector among those available is not necessarily intuitive.

A robust sensing vector selection method is desirable, as well as devices adapted to perform such methods. The present invention, in illustrative embodiments, provides such methods and uses various criteria for doing so. Some embodiments include implantable devices and programmers for implantable devices that are adapted to perform such methods.

The systems shown in FIGS. 1A-1B may include operational circuitry and a power source housed within the respective canisters. The power source may be, for example, a battery or bank of batteries. The operational circuitry may be configured to include such controllers, microcontrollers, logic devices, memory, and the like, as selected, needed, or desired for performing the illustrative methods set forth herein. The operational circuitry may (although not necessarily) further include a charging sub-circuit and a power storage sub-circuit (for example, a bank of capacitors) for building up a stored voltage for cardiac stimulus taking the form of cardioversion and/or defibrillation. The operational circuitry may also be adapted to provide a pacing output. Both cardioversion/defibrillation and pacing sub-circuitry and capacities may be incorporated into a single device. The methods discussed below may be embodied in hardware within the operational circuitry and/or as instruction sets for operating the operational circuitry and/or in the form of machine-readable media (optical, electrical, magnetic, etc.) embodying such instructions and instruction sets.

Each of the devices 12, 32 may further include such components as would be appropriate for communication (such as RF communication or inductive telemetry) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate and/or direct and/or observe diagnostic or operational tests. After implantation, the programmer 24, 42 may be used to non-invasively determine the status and history of the implanted device. The programmer 24, 42 and the implanted devices 12, 32 are adapted for wireless communication allowing interrogation of the implanted device(s). The programmers 24, 42 in combination with the implanted devices 12, 32 may also allow annunciation of statistics, errors, history and potential problem to the user/physician.

In some embodiments, the following illustrative methods are performed directly by the implanted devices 12, 32 either independently (periodically or occasionally) or at the direction of a programmer 24, 42. In other embodiments, the following methods are performed by using the implanted devices 12, 32 to perform data capture, with the programmer 24, 42 performing other analytical steps by downloading captured data (for example, in real time, or in blocks of predetermined size). The programmer 24, 42 may prompt additional data capture as suitable for the illustrative methods below, and the programmer 24, 42 may then direct the implanted devices 12, 32. Some methods may be performed by distributing appropriate tasks between the implanted devices 12, 32 and the programmer 24, 42.

Figure 2:
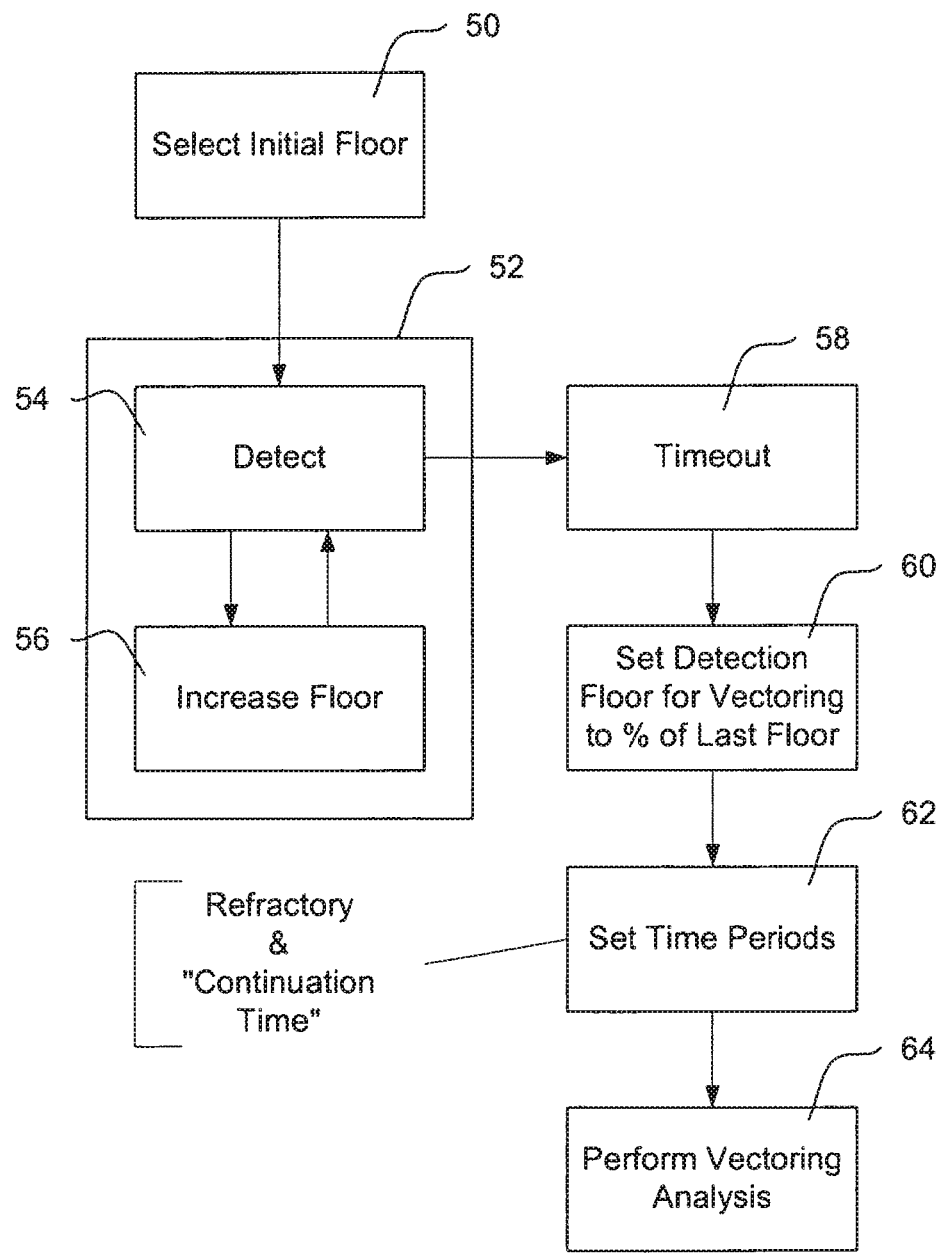
FIG. 2 is a block diagram illustrating a method of initialization for an implantable cardiac stimulus system.

FIG. 2 is a block diagram illustrating a method of detection initialization for an implantable cardiac stimulus system. For the vectoring method, a detection threshold for the implantable cardiac stimulus system is initialized by performing a process of detection with one or more available sensing vectors. For example, the method steps shown in FIG. 2 may be performed for sensing vectors A-Can, B-Can, and A-B, shown in FIGS. 1A-1B. The steps may also be performed using vectors including the shocking/coil electrode 18 shown in FIG. 1A as well as any stimulus electrodes in FIG. 1B, although the set under consideration is reduced for illustrative purposes in the following examples to A-Can, B-Can, and A-B.

A vectoring method is a method of analyzing one or more available sensing vectors to select a sensing vector for use in detection. The method in FIG. 2 is used to set the sensing parameters for a vectoring method. FIG. 2 includes first setting an initial sensing floor, as shown at 50, preferably in a relatively low range (high sensitivity) so that the device will detect cardiac events that exceed the detection floor. For example, this initial sensing floor may be set to a percentage of a historical value measured over a number of previously detected cardiac events, specific to the patient, a patient population, a particular implantation configuration, or other suitable variables.

As shown at block 52, several iterations of a sub-method are performed. In block 52, an event is detected, as shown at 54, and the detection floor is then raised, as shown at 56. The event detection 54 may occur when the detection floor is crossed by the sensed signal, and may include a refractory period during which detection is disabled. Iterations in block 52 may continue until a timeout occurs, as shown at 58. The timeout 58 may occur, for example, when a 2-second period of time expires without a detection occurring. The timeout may indicate the detection floor has been raised above the received signal strength for cardiac events.

After the timeout at 58, the vectoring detection floor is set to a percentage of the detection floor that led to the timeout 58, as shown at 60. For example, the vectoring detection floor may be set to about 40% of the level that led to the timeout. Next, time periods are set, as shown at 62, and vectoring analysis is performed as shown at 64. The time periods are explained by reference to FIGS. 3A-3B. The vectoring detection floor may be set differently for each of the sensing vectors being analyzed, since each vector may produce a different signal strength than the other vectors. For example, the method shown in FIG. 2 may be repeated for each of several vectors prior to performing any vectoring analysis 64, or the method of FIG. 2 may be performed as a part of vectoring analysis for each individual vector.

FIG. 3A is a graphical representation of a cardiac signal illustrating an analytical form for identifying QRS and T-Waves. A cardiac signal is shown at 80. A vectoring detection threshold is shown at 82. An event is detected at 84, when the cardiac signal 80 crosses the vectoring detection threshold 82. A refractory period 86 occurs following the detection 84. After the refractory period 86, a continuation time (CT) period occurs, as shown at 88. The peak occurring during the refractory period 86 is at least initially assumed to be the R-wave, as shown at 90. A peak signal value is identified during the CT period, as shown at 92, and is assumed to be noise. This peak 92 may be the T-wave, but is not necessarily so. In an illustrative example, the refractory period 86 lasts 160 milliseconds, and the CT period 88 lasts 220 milliseconds, although these values may vary in other embodiments.

In the illustrative example, it is assumed (for vectoring purposes) that the longest QT interval will be about 400 milliseconds, and so the peak value detected during the CT period 88 is assumed to be the T-wave. The illustrative method, with the parameters given above, is adapted for use with a patient having a heart rate of 30-150 beats-per-minute (bpm). The detection threshold 82 is effective during the CT period 88, such that, if the sensed signal crosses the detection threshold 82 during the CT period 88, this will be treated as another detection.

Figure 3B:
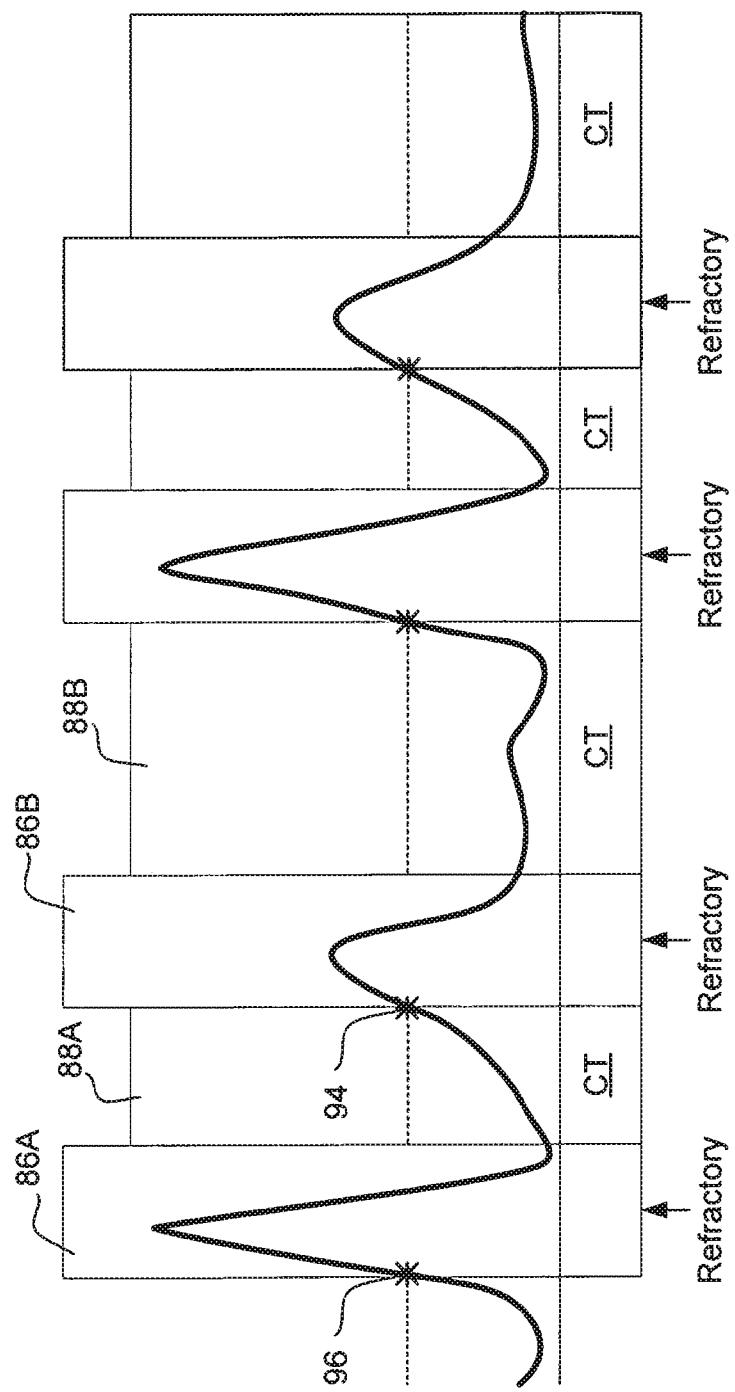

FIG. 3B illustrates that a new detection 94 will be defined for a threshold crossing during the CT period 88A that follows a first refractory period 86A associated with a first detection 96. The new detection 94 has its own refractory period 86B and CT period 88B. Given a rate of 150 bpm or less, the detections shown in FIG. 3B indicate a double detection, as the detections are too close together. It can be seen that, when double detection occurs, sensing outside of the CT periods 88A, 88B may not happen, although this is not always the case. As explained further below, the present methods are adapted to select at most one of the detections 94, 96 as representative of a heart beat, while determining that the other detection 94, 96 is noise.

Because the different sensing vectors may detect events in different forms, and because the targeted population for such devices often has abnormal cardiac function, a prototypical PQRST form, as shown in FIG. 3A, may not always occur. For example, the T-wave may be relatively larger than the R-wave. Some of the present methods also include an ability to set a flag that calls for an attending physician (the "operator") to observe the cardiac signal and determine whether the R-wave or T-wave has a greater amplitude. When certain conditions are met, the flag is set and the operator may be asked for input.

Figure 4:
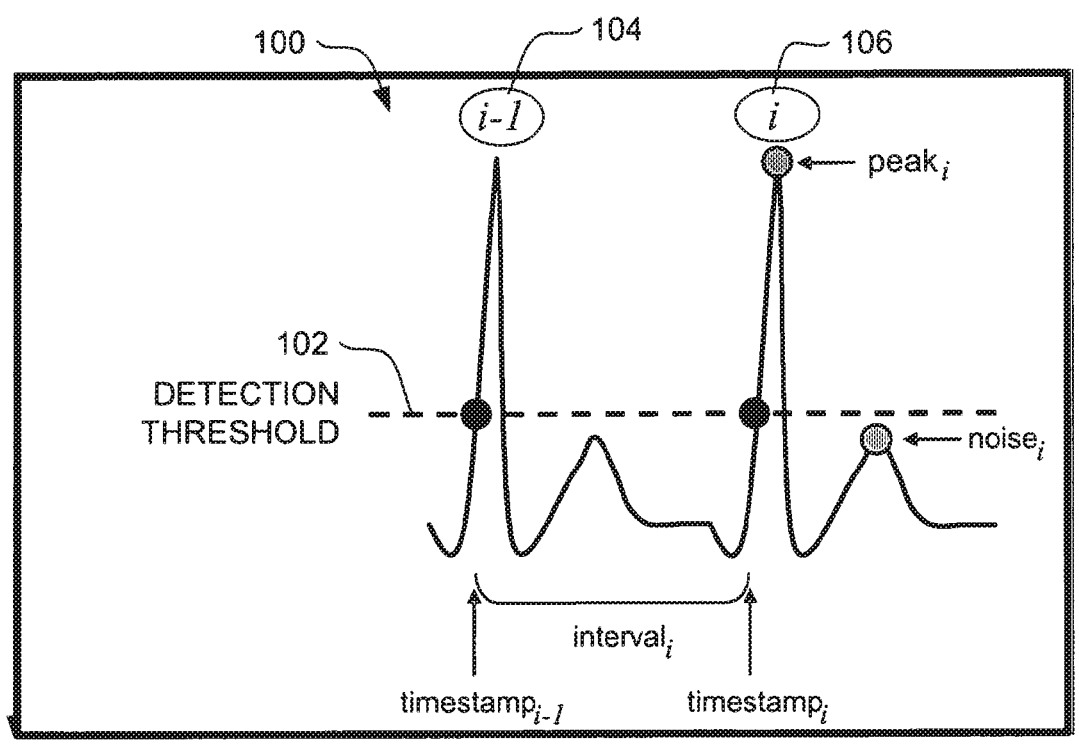
FIG. 4 is a graph showing treatment of a cardiac signal for explanatory purposes.

FIG. 4 is a graph showing treatment of a cardiac signal for explanatory purposes. During the vectoring example that follows, the captured cardiac signal is marked to identify events. The signal, shown at 100, is detected relative to a detection threshold 102. When the signal exceeds the detection threshold, this is marked as an event. The chronologically most recent event is marked event i, as shown at 106, while a contiguously prior event is marked i−1, as shown at 104. The duration of time between detections 104 and 106, is defined as interval$_i$, while the height of peak 106 is amplitude$_i$, and the height of the noise peak following peak 106 is noise$_i$. One goal is to define the detected events and portions of the cardiac signal in a manner as shown in FIG. 4; the methods of FIGS. 5A-5B, as well as other methods shown below, are adapted to achieve this goal, when possible.

Figure 5A:
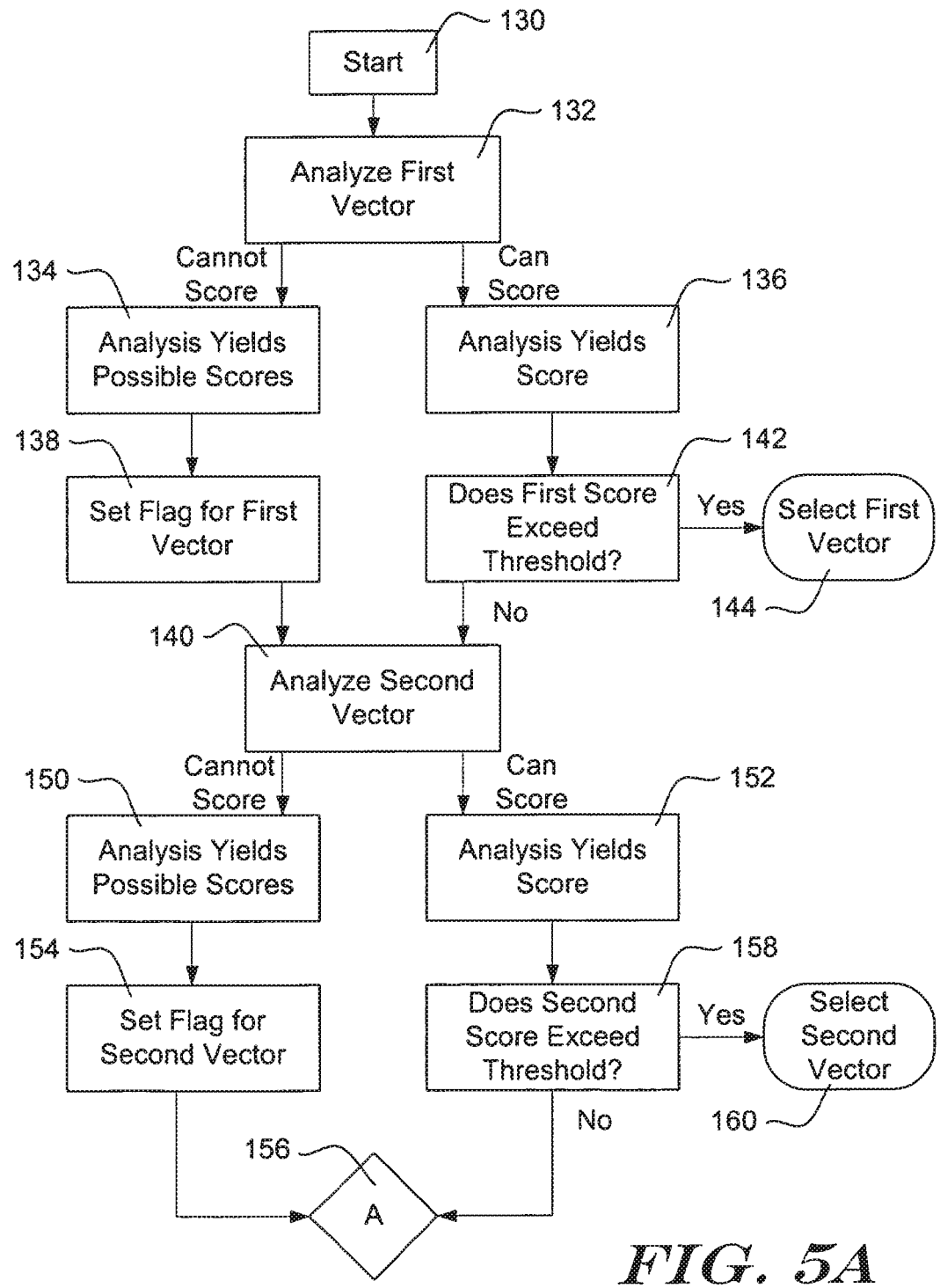
FIGS. 5A-5B illustrate a block diagram for a method of signal vector analysis.
Figure 5B:
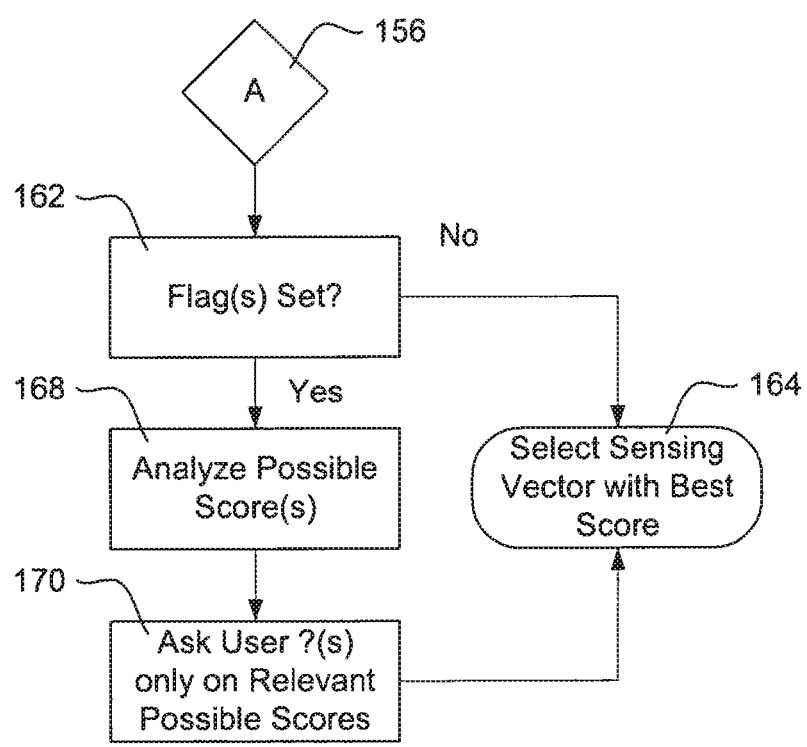

FIGS. 5A-5B illustrate a block diagram for a method of sensing vector analysis. The illustrative method starts as 130. A first vector is analyzed, as shown at 132. The details of analysis are further explained elsewhere. This analysis may include performing the method of FIG. 2, or the thresholds defined in FIG. 2 may be defined prior to performing the method for the first vector or more vectors. The analysis may provide a Score, as shown at 136, or cannot provide a Score, and instead provides Possible Scores, as shown at 134.

The use of "Score" and "Possible Scores" terms should be explained. In an illustrative example, the vectoring analysis observes parameters of the sensed cardiac signal to determine whether the signal is likely useful for cardiac event detection. In an illustrative example, interval analysis is used to determine whether "good" detections are occurring. A "good" detection may have a desirable range of signal-to-noise ratio and/or amplitude, and may avoid detecting undesired "events" (artifacts). If the interval analysis indicates regular detections are occurring, and early detections are not occurring, a Score is calculated for the sensing vector. The Score is an example of a metric for the received signal that indicates the quality of the sensing vector for cardiac event detection purposes.

If the interval analysis does not, with certainty, parse out noisy detections from actual cardiac event detections, then two or more Possible Scores may be calculated, each based on an assumed resolution of the ambiguity or uncertainty that prevents calculation of a score without ambiguity. For example, two Possible Scores may be calculated, one assuming the QRS peak exceeds the T-wave or other noise peak, and the other assuming the QRS peak does not exceed the T-wave or other noise peak. The following illustrative examples utilize a particular calculation of Scores and Possible Scores for sensing vectors, the details of which may be modified in various suitable ways. It is sufficient that the Score or other metric provide an indication of the quality of the signal captured along a sensing vector for purposes of cardiac event detection and/or analysis.

Returning to the example in FIG. 5A, if the analysis yields only Possible Scores, as indicated at 134, a question flag is set for the first vector, as shown at 138. The question flag indicates that the operator may need to provide input to the vectoring process to determine which of the Possible Scores is the correct Score to use for the first vector by observing whether "QRS>T-wave?". However, rather than immediately asking the operator's assistance, the method instead analyzes the second vector, as shown at 140.

Returning to step 136, if a score is provided for the first vector, the method next determines whether the score for the first vector exceeds a predetermined threshold, as shown at 142. In the illustrative method, if the threshold is exceeded, this indicates that the first vector provides excellent sensing, and further analysis is deemed unnecessary. Therefore, if the threshold is exceeded for the first vector, the method ends by selecting the first vector, as indicated at 144. Otherwise, the method goes on to analyze the second vector, as shown at 140. Thus, the method tests sensing vectors in a preferential order with vectors that are less likely to yield high-quality results being tested after other, often more favorable vectors have been tested.

As with the first vector, analysis of the second vector either yields a Score, as indicated at 152, or cannot yield a score and instead provides Possible Scores, as shown at 150. If Possible Scores are provided, the question flag is set for the second vector, as shown at 154. The method then goes to A, as shown at 156, which continues in FIG. 5B.

If, instead, analysis of the second vector yields a Score, the method continues from block 152 to determine whether the Score for the second vector exceeds a threshold, as shown at 158. Again, if the threshold is exceeded, this indicates the second vector provides excellent sensing and so the method ends by selecting the second vector, as shown at 160. Otherwise, the method continues to A 156 in FIG. 5B. The steps shown for the first and second vectors may be repeated for any number of vectors, depending upon the particulars of the implantable cardiac stimulus system.

Referring to FIG. 5B, from A 156, the method determines whether any of the question flags have been set, as shown at 162. If not, the method simply selects the sensing vector with the best Score, as shown at 164. If one or more flags have been set, the method continues at 168 by analyzing the Possible Scores. The operator (the attending physician) may be asked questions regarding any of the relevant Scores or Possible Scores.

The analysis at 168 may include determining whether any questions need to be asked. For example, if at least one vector yields a Score, and none of the available Possible Scores from other vectors exceed the highest Score, the operator is not asked any question, since the Possible Scores cannot provide the best available vector. Further, the operator may be asked only relevant questions by selecting the vector having the best Possible Score first. The operator is asked the question(s), as shown at 170. If the operator answer eliminates the best Possible Score, the method may iterate to ask additional questions relative to one or more next-best Possible Scores. Or, if the answer eliminates the best Possible Score, and the remaining highest score is a Score, rather than a Possible Score, a corresponding sensing vector is selected. Then, the sensing vector with the best Score is selected, as shown at 164.

It should be noted with respect to FIGS. 5A-5B that the portion of the method shown in FIG. 5A selects a vector depending on whether the vector provides a sufficient Score. The portion of the method in FIG. 5B, on the other hand, selects the vector with the best Score.

In some embodiments, both first and second sensing vectors are selected, with the first sensing vector being a primary or default sensing vector and the second sensing vector being an alternative or clarifying vector. For example, during a given cardiac episode, if the first vector provides at best ambiguous indications of whether therapy is needed, the second vector may be used to resolve any ambiguity. In other embodiments, a second sensing vector may be identified during the initialization procedure in case, at a later time, the first sensing vector becomes unsuitable (due to changes in physiology, external noise, etc.) or unavailable (due to mechanical failure, for example). For embodiments identifying first and second sensing vectors, the method of FIGS. 5A-5B may simply continue, using similar steps and processes, until a second vector is identified in like fashion.

Figure 6:
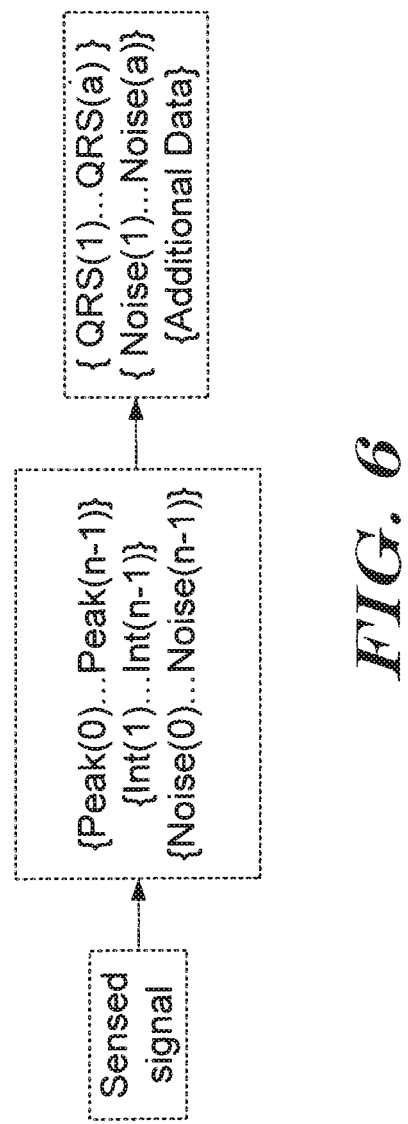
FIG. 6 illustrates a simplified model of an illustrative method.

An illustrative method is shown by FIG. 6. A sensed signal is parsed using detection techniques into various significant features including, for example, peak amplitudes, intervals between peaks, and noise levels between peaks. FIG. 5 illustrates an analytical form for this first step. Next, the features identified by the detection techniques are further analyzed to reduce the number of variables under consideration. In the illustrative example of FIG. 6, a set of {n} detected events is analyzed to generate a set of {a} identified QRS peaks and associated noise levels, where the only known relationship between n and a is that n>a. Because the sensed signal may not readily parse and condense into the data pairs shown, allowance is made for ambiguity during signal processing by carrying forward "additional data" as well. If necessary, the implications of the "additional data" may be determined by seeking user input, as further set forth below.

Figure 7A:
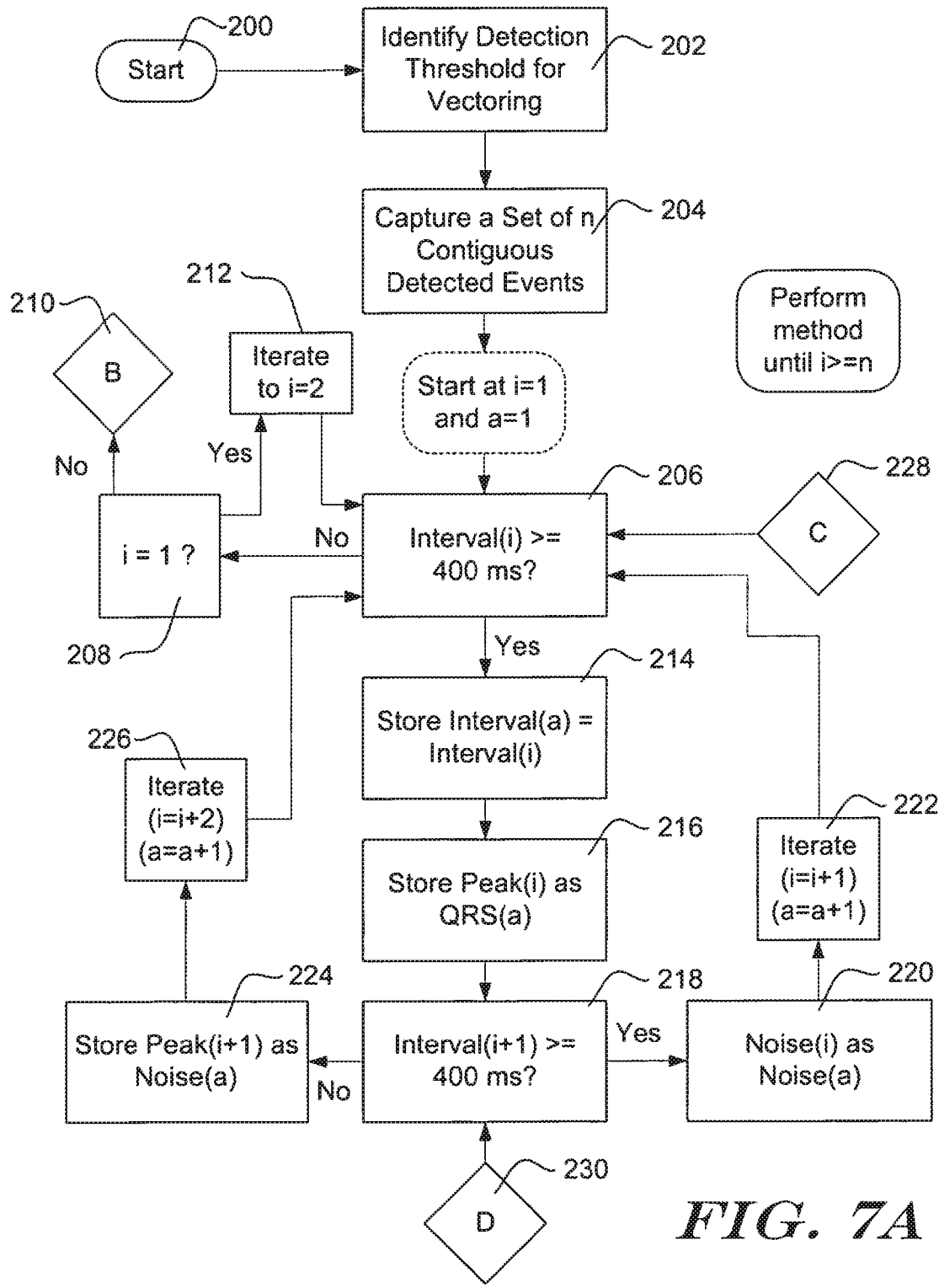
FIGS. 7A-7B illustrate a block diagram for a method of signal analysis within the vector analysis of FIGS. 5A-5B.
Figure 7B:
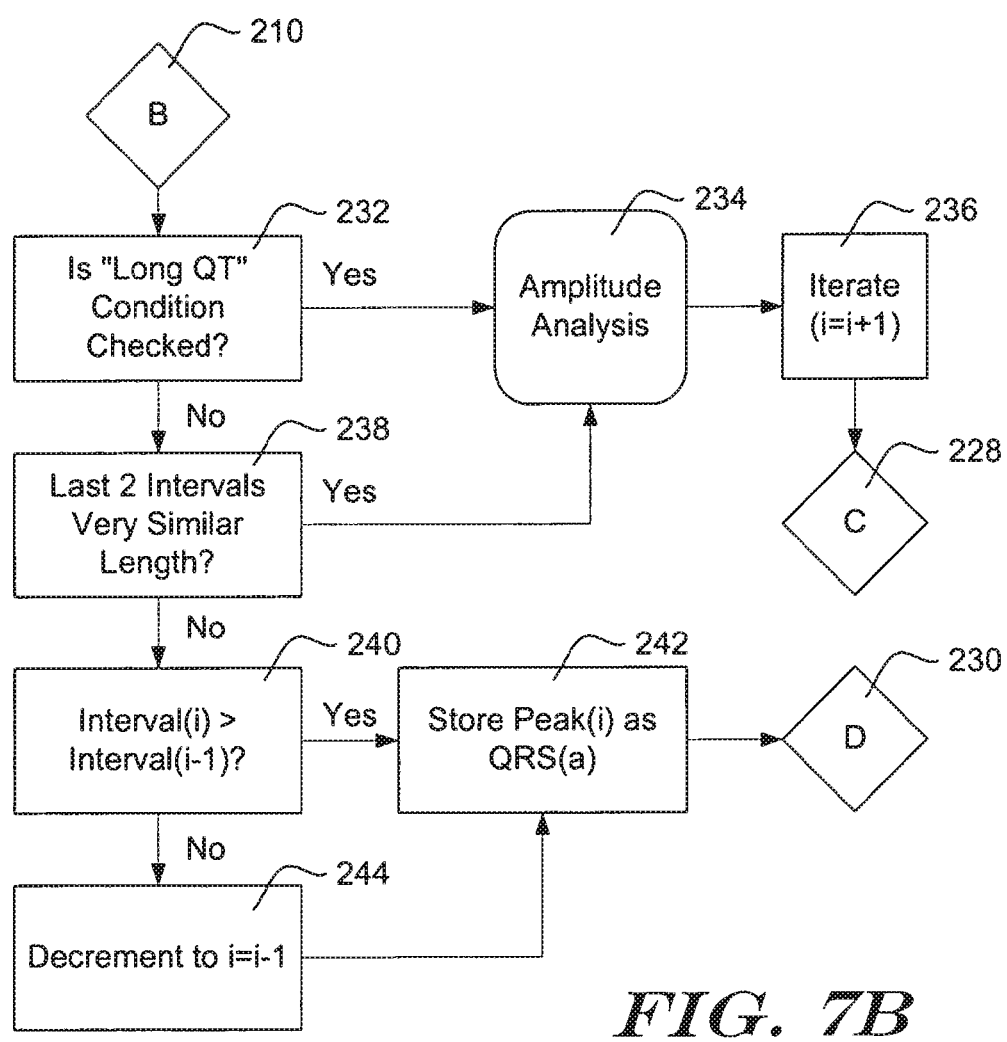

FIGS. 7A-7B illustrate a block diagram for a particular form of the method of FIG. 6. The method illustrated in FIGS. 7A-7B is a particular form for transferring data related to a sensing vector into metrics for evaluating the merits of a given sensing vector against one or more thresholds and/or other sensing vectors. From start block 200, the method identifies a detection threshold for vectoring, as shown at 202. In some embodiments, step 202 may be achieved by the method of FIG. 2, for example. Next, the illustrative method captures {n} contiguous detected events, as indicated at 204. The "detected events" may occur when the detection threshold is crossed by the sensed signal. Selected data samples associated with the detected events are also kept for analysis. In an illustrative embodiment, n=11, although other larger or smaller sets of events may also be used. An iterative analysis follows for events marked initially with the i variable, with the iterative method continued until i>=n, although in some embodiments the method may abort if it becomes clear that the vector being considered is unsuitable. For the first iteration, coming from block 204, the method uses i=1 and also sets another variable a=1.

The loop then starts for the {n} detected events by considering the interval between a first (i−1) event and a second (i) event. As shown at 206, an interval between the $i^{th}$ event and the i−$1^{th}$ event, Interval(i), is compared to a threshold, with 400 milliseconds used for illustrative purposes. If the threshold is not exceeded, the method continues at B, as shown at 210, in FIG. 7B, unless, as indicated at step 208, the first interval was being considered (Interval(1), in which case the method simply iterates to i=2, as shown at 212, and loops back to step 206 again. If, at 206, the interval is greater than the threshold, then the interval is stored as Interval(a), as shown at 214, and the peak captured during the $i^{th}$ refractory period is stored as QRS(a), as shown at 216.

The interval between i and i+1 (Interval(i+1)) is then considered as shown at 218, and compared to a threshold, which is again shown for illustrative purposes, as 400 milliseconds. If, at 218, the threshold is exceeded, then the peak signal captured during CT(i), the continuation time that follows refractory for the $i^{th}$ detection, is stored as Noise(a), as indicated at 220. The method then iterates as shown at 222, and returns to step 206 but with i=i+1 and a=a+1.

Returning to step 218, if the $(i+1)^{th}$ interval considered there does not exceed the threshold, then the refractory peak that caused the latter detection is stored as Noise(a), as shown at 224. This occurs because it is assumed that the latter detection occurred too close to the prior detection to be another QRS complex. The illustrative 400-millisecond threshold interval is used in association with a method that should be performed when the patient's heart rate is in the range of about 30 to 150 beats-per-minute (bpm). Detections occurring with less than a 400-millisecond interval would correspond to a higher beat rate (150 bpm or more), and therefore the method assumes that shorter intervals indicate one or more detections are caused by noise. The methods may be tailored to other patient beat rates, if desired.

From 224, the next iteration starts at 226 after another iteration, this time with i=i+2 and a=a+1. The i variable receives a double iteration since, as shown at 224, the $(i+1)^{th}$ peak is considered to be noise. When returning to step 206, in some embodiments the next interval is taken from i−2 to i, spanning the i−1 event that has been identified as likely occurring due to noise. For example, at a microcontroller level, a flag may be set to indicate double iteration at step 226, the flag being reset once the interval is considered in step 206.

Turning now to FIG. 7B, the method picks up at block B 210, which continues from block B 210 in FIG. 7A. As shown at 232, the method continues by determining whether a "Long QT" condition has been checked. In an illustrative embodiment, the "Long QT" condition allows an operator to indicate to the implantable device system and/or the programmer that the patient is susceptible to a long interval between the Q and T signals. For such a patient, the T-wave is likely to occur rather late after the R-wave in the overall cardiac cycle. By reference to the analysis using a refractory period and CT interval, as shown in FIG. 3A-3B, a "Long QT" patient may experience the T-wave after expiration of the CT interval. This may cause the detection circuitry to detect a threshold crossing due to the T-wave artifact after the CT time period expires in one or more sensing vectors.

If the "Long QT" condition is checked, the method continues with amplitude analysis, as indicated at 234. An illustrative method of amplitude analysis 234 is further explained below by reference to FIGS. 8 and 9A-9C. After amplitude analysis at 234, the method iterates using i=i+1, and returns to block C 228 in FIG. 7A, which ultimately sends analysis to block 206. It should be noted that the {a} variable is not iterated here, as the data elements QRS(a) and Noise(a) have not been filled with data during amplitude analysis at 234.

If the "Long QT" condition is not checked at block 232, the method determines whether Interval(i−1) and Interval(i) are very similar in length. In an illustrative example, the intervals are considered to be very similar in length when their durations are within 50 milliseconds of one another, for example, 300 milliseconds is considered very similar in length to 320 milliseconds, although the exact parameters for determining similarity may vary. If the intervals are very similar in length at 238, the method continues with amplitude analysis, as shown at 234, as before.

If the intervals compared at 238 are not similar, the method determines whether Interval(i) is longer than Interval(i−1), as shown at 240. If so, then Peak(i) is stored as QRS(a), as shown at 242. Otherwise, if Interval(i−1) is not shorter than Interval(i), the method decrements the {i} variable to i=i−1, as indicated at 244, and continues to step 242. Using either course, the method continues from step 242 to D, as shown at 230, which returns to FIG. 7A, directing the method to step 218.

Figure 8:
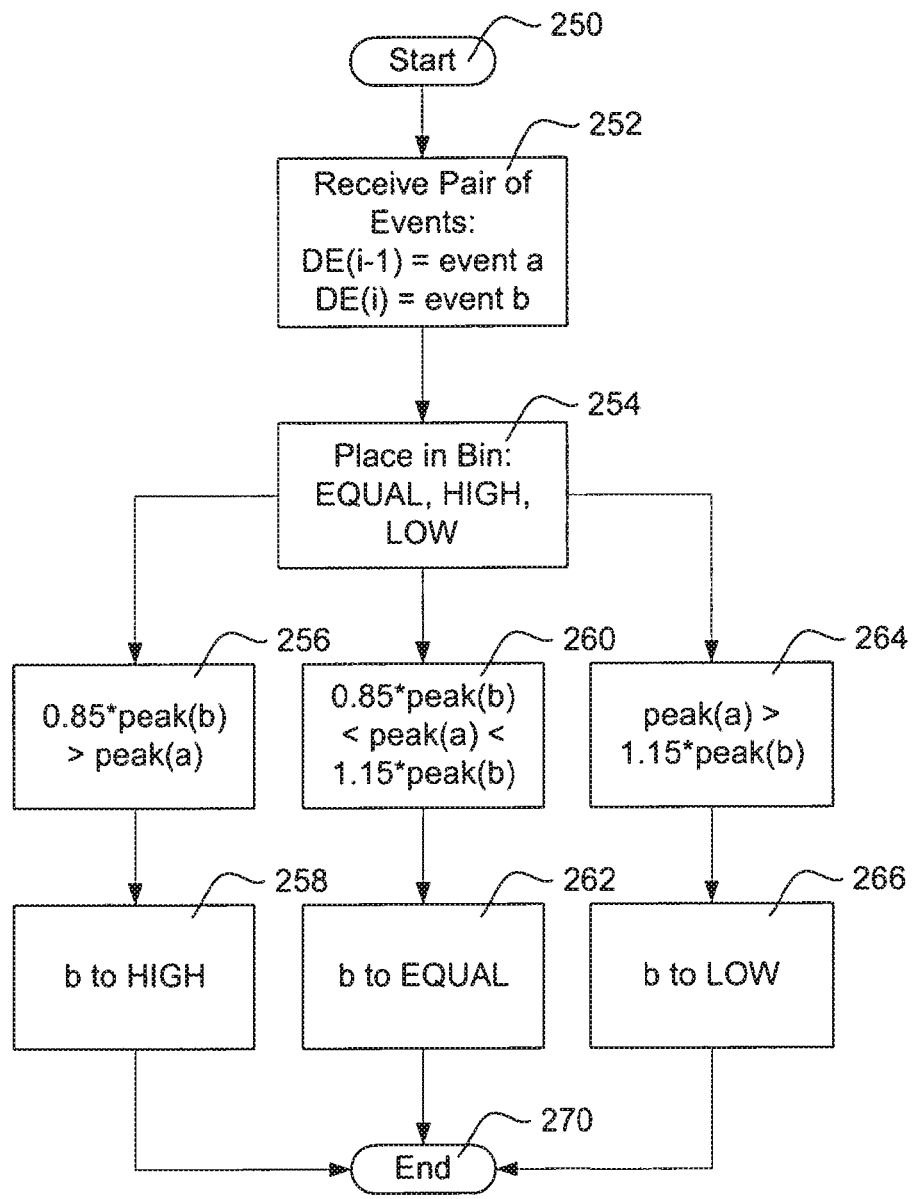
FIG. 8 illustrates a block diagram for a method of assessing cardiac signal quality.

Detected events that are analyzed in FIGS. 7A-7B and found to be QRS events are placed in a QRS bin, while events that are found to be noise are placed in a Noise bin. Those events that undergo amplitude analysis are placed in bins as illustrated in FIG. 8. In some embodiments, the method may be aborted if too many events are placed in bins for amplitude analysis, although this is not necessarily the case.

FIG. 8 illustrates a block diagram for a method of assessing cardiac signal quality. This method may be a part of the amplitude analysis 234 shown in FIG. 7B. From start block 250, the method receives a pair of events a and b, as shown at 252. Event b is to be placed in one of several bins, as indicated at 254, depending upon the relative amplitudes of events a and b. More particularly, if the amplitudes of peaks a and b are more or less equal, within +/−15% margin, event b is placed in the EQUAL bin, as shown at 260, 262. If peak b is larger than peak a, outside of the margin for the two being equal, then b is placed in the HIGH bin, as shown at 256, 258. Conversely, if peak a is much greater than peak b, then b is placed in the LOW bin, as shown at 264, 266. The binning process of FIG. 8 is used later in FIGS. 9A-9C.

Figure 9A:
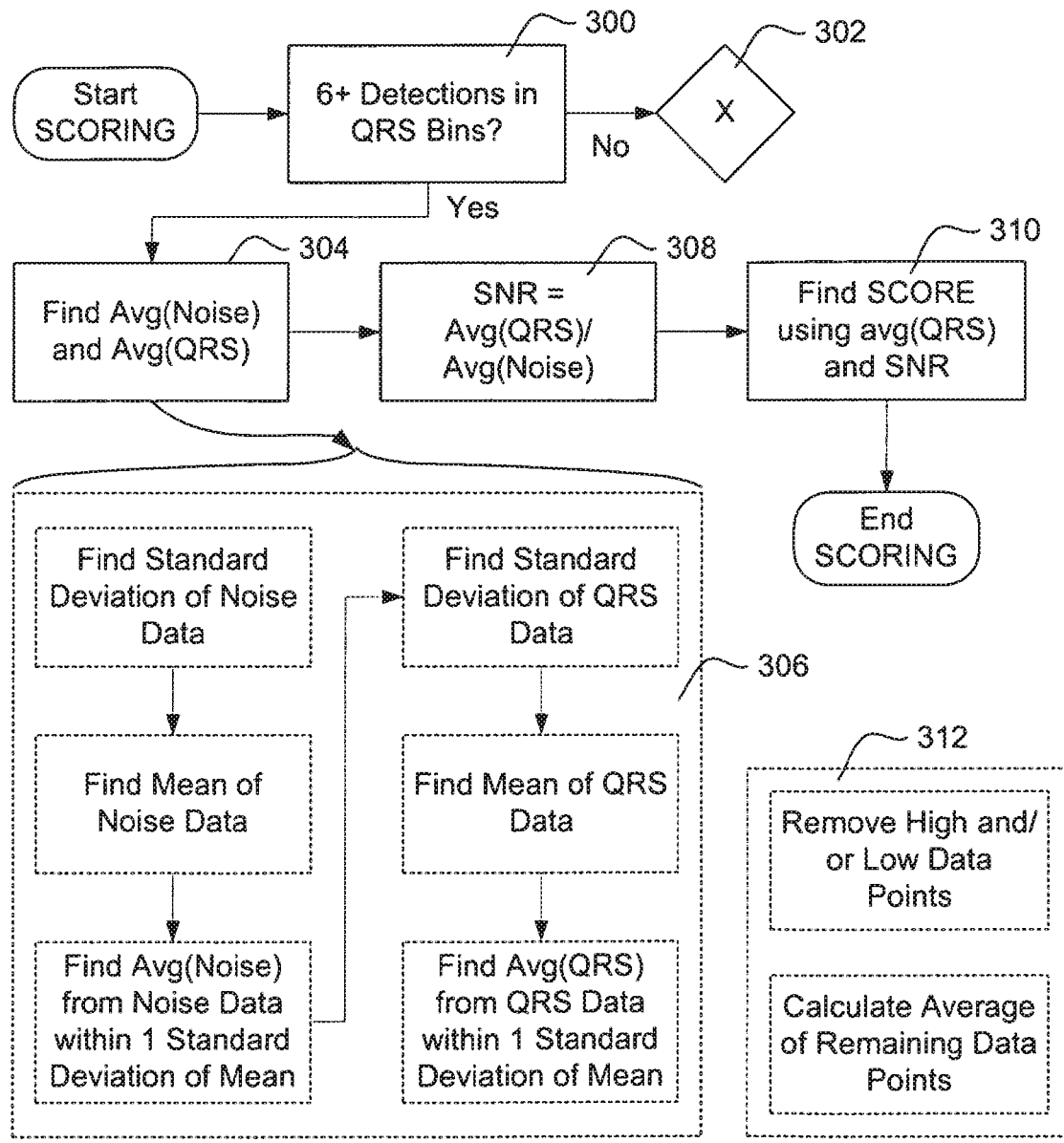
FIGS. 9A-9C illustrate a block diagram for a method of analyzing a cardiac signal.
Figure 9B:
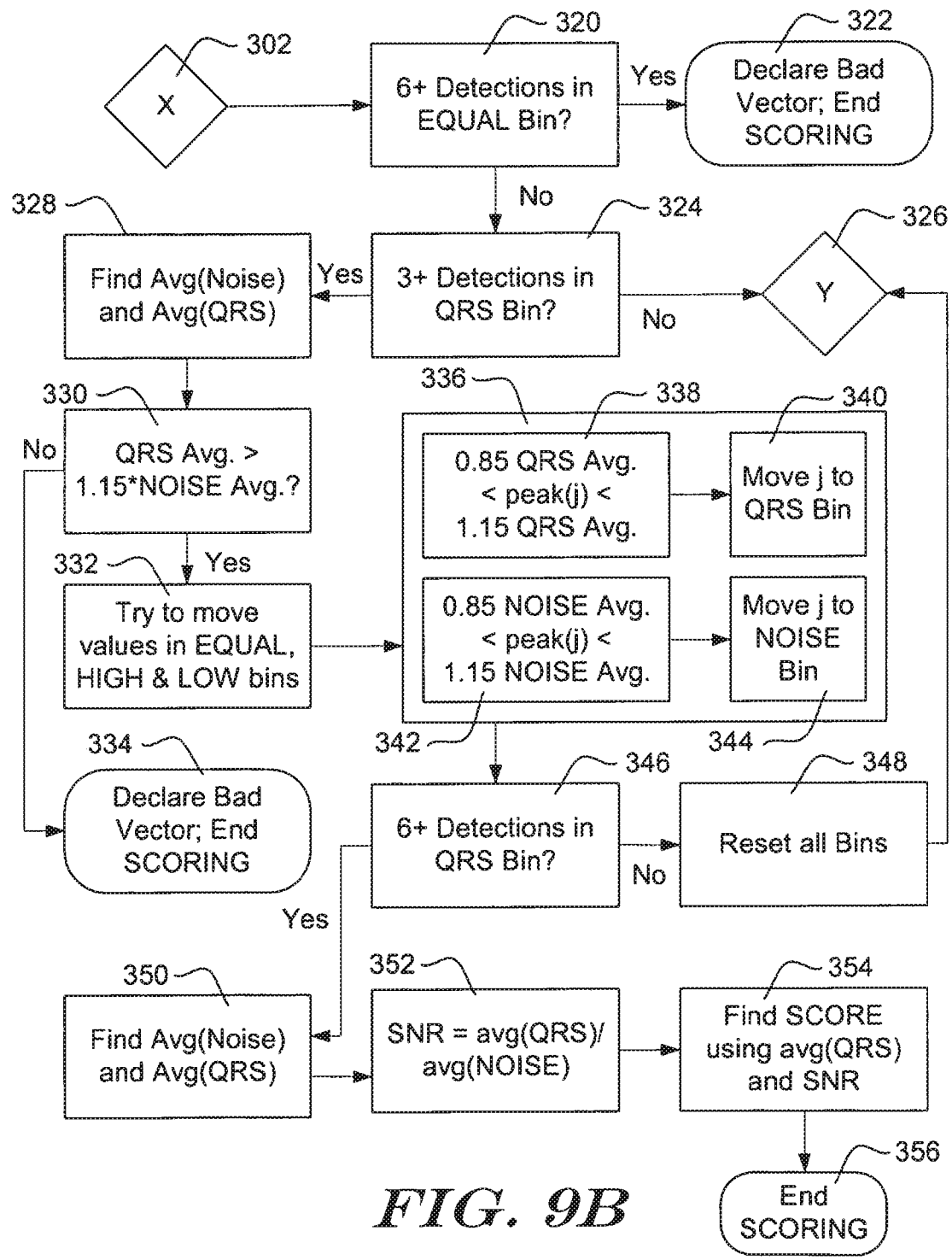
Figure 9C:
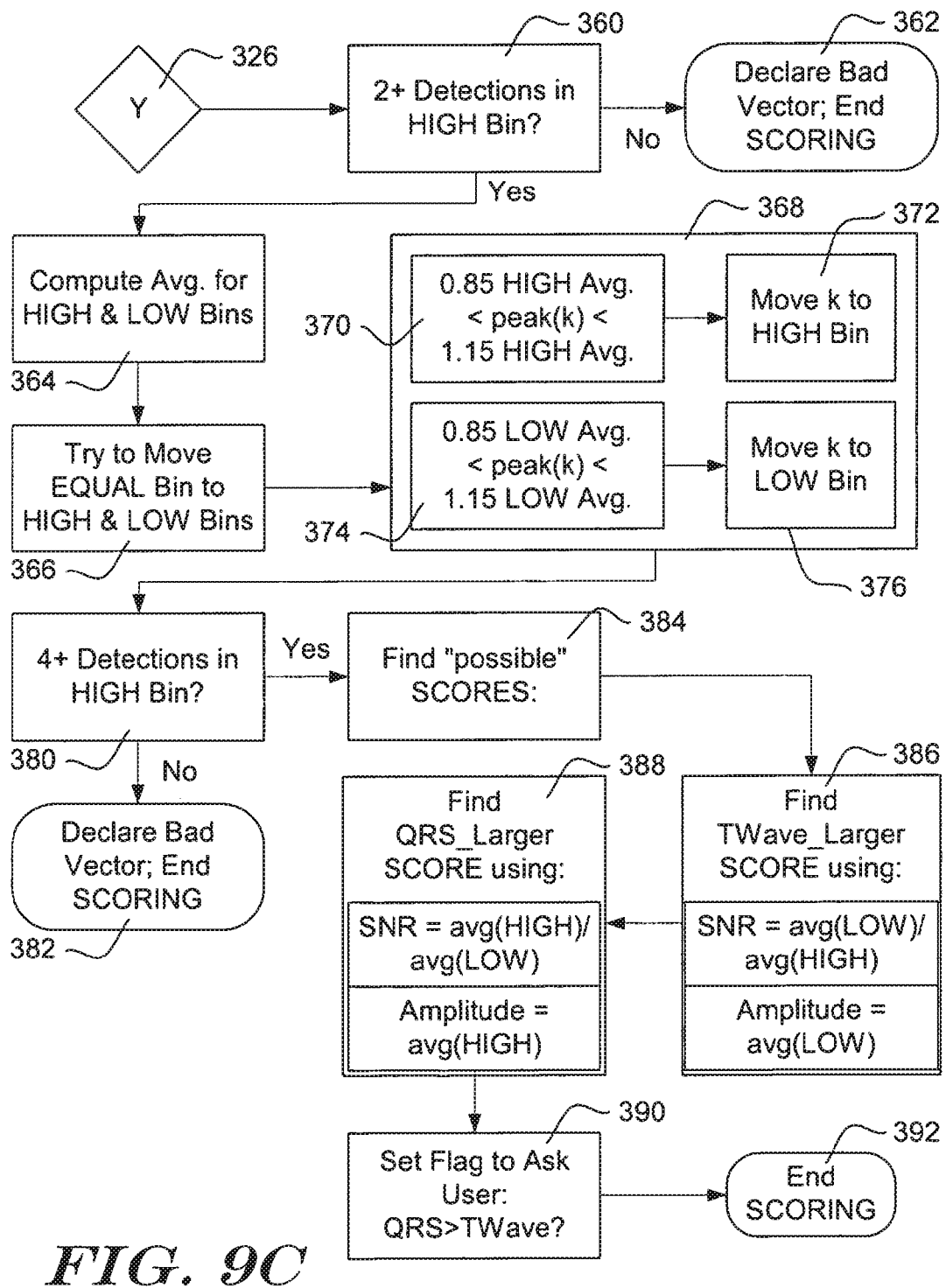

FIGS. 9A-9C illustrate a block diagram for a method of analyzing a cardiac signal. The method of FIGS. 9A-9C is a method for calculating a Score for a given vector. The method assumes the use of the methods of FIGS. 7A-7B to analyze {n} contiguous detected events. These events, as explained above, may generate paired Noise and QRS data elements, which are separated and placed in a QRS bin and a NOISE bin. Also, with the amplitude analysis of FIG. 8, some events related to ambiguous intervals may be placed in bins for HIGH, LOW and EQUAL.

For illustrative purposes, the example of FIGS. 9A-9C uses n=11 as the number of initially detected events. In other embodiments, any suitable number of events may be used. The parameters used in the following example are merely illustrative of one manner of performing the method, and may be modified to suit other systems, specific circumstances, or variables. The method of FIGS. 9A-9C begins at a start block, and determines whether 6 or more of the n=11 detections have been placed into the QRS bins, as shown at 300. If not, the method continues with block X 304 in FIG. 9B.

If there are 6 or more detections in the QRS bin, then the average amplitudes for noise and QRS bins are calculated, as shown at 304. An illustrative method of performing this calculation is shown in block 306. The standard deviation is determined for the noise data, as well as the mean. Then the average is calculated by excluding any outlying data (illustratively, data that falls outside of one standard deviation of the mean). The process is repeated for the QRS data as well. Alternatively, the method shown in block 312 may be used instead to calculate averages for one or both of Noise and QRS data. In this somewhat simpler method, a highest data point and/or a lowest data point are removed from the data set and the average is calculated using the reduced data set, as shown at 312.

The SNR is then calculated as the ratio of the average amplitude of the remaining events in the QRS bin to the average of the amplitudes stored in the NOISE bin, as shown at 308. Next, the SCORE is calculated using the average amplitude of the remaining events in the QRS bin along with the SNR, as shown at 310. In an illustrative example, the following lookup table is used to find the SCORE:

| LOOKUP TABLE | | | |
| --- | --- | --- | --- |
| $S_A$ | Amplitude Range (mV) | $S_R$ | SNR |
| 0.5 | ≤0.5 | 0.5 | ≤3 |
| 5 | 0.5-0.65 | 1 | 3-3.5 |
| 10 | 0.65-0.8 | 25 | 3.5-4 |
| 18 | 0.8-1.0 | 50 | 4-5 |
| 30 | 1.0-1.7 | 75 | 5-7.5 |
| 20 | 1.7-2.0 | 100 | >7.5 |
| 40 | 2.0-3.0 | | |
| 15 | 3.0-3.5 | | |
| 0.5 | 3.5-4.0 | | |

The illustrative lookup table is adapted for a system in which the device is adapted to sense with either a LOW or HIGH amplitude input, having dynamic ranges of either ±2.0 millivolts or ±4.0 millivolts. For this illustrative system, peak amplitudes in the 1.7-2.0 millivolt range create a likelihood of clipping and/or difficulty in using only one of the two dynamic ranges all the time. Likewise, peak amplitudes in the range of 3.5-4.0 millivolts create a likelihood of clipping as well, making this a less preferred range such that a lower SA factor is provided. The lookup table may be adapted for other systems having different characteristics.

In some embodiments, the dynamic range of the analysis system for use in association with the vector under consideration may be set depending upon the average value found and/or the mean of the QRS data. For example, the method may include selecting a dynamic range for the analog-to-digital converter, incoming signal amplifier, or other component(s) of the system.

Next, the Score is determined from:

$$S_A * S_R = \text{Score}$$

With the score calculated at 310, scoring is complete, and the method ends.

In an illustrative embodiment, the above scoring chart is used in association with the method of FIGS. 5A-5B with the thresholds for selecting one of the first or second sensing vectors being set at 1750. For example, a calculated amplitude of 2.2 volts, with an SNR of 4.5, would score 2000, sufficient to have a sensing vector automatically selected without further consideration of other vectors. These parameters may be adjusted in light of system capabilities and/or requirements. In other embodiments, rather than a scoring chart, a formula may be used.

Turning now to FIG. 9B, the method picks up at block X 302, coming from FIG. 9A. The method determines whether there are 6 or more (again, out of 11, although these numbers may be varied) detections in the EQUAL bin, as indicated at 320. If so, the sensing vector under consideration is yielding too many ambiguous results and too much noise, causing overdetection that the system has a difficult time resolving. Therefore, the sensing vector is declared bad, as shown at 322, and the scoring method ends as no Score can be returned for the vector under consideration. The overall vectoring method would, at this point, continue analysis with a different sensing vector.

If the condition at 320 is not true, then it is determined whether there are at least 3 of 11 detections in the QRS bin, as indicated at 324. If not, the method continues at block Y 326 and on to FIG. 9C. If there are 3 or more detections in the QRS bin, the method continues at 328, the Average for NOISE and QRS are each calculated. This may be performed in accordance with one of the methods of blocks 306 or 312 of FIG. 9A, although, due to the reduced data set initially under consideration, the method of block 312 may be more useful, as the statistical analysis of block 306 is less useful.

Next, the QRS Average and NOISE Average are compared to one another to verify that the bins contain values that are separated from one another, as shown at 330. The use of 1.15 as a multiplier is merely illustrative of one form of this comparison. In another embodiment, rather than a multiplier, an offset having a stable value is used, or a formula such as Ax+B may be used, with A as a multiplier and B as an offset. Other comparisons may also be made to determine separation. If the values in the QRS and NOISE bins are too close to one another, the method jumps to step 334, where a bad vector is declared and scoring ends.

If the condition at 330 is met, the remaining values in the EQUAL, HIGH and LOW bins are analyzed to see which, if any, can be moved to one of the QRS or NOISE bins, as indicated at 332. The data points in the EQUAL, HIGH and LOW bins are moved to QRS and/or NOISE by the method steps shown in block 336. For each data point, j, the peak amplitude is compared to see if it may fit in one or the other of the QRS or NOISE bins due to its amplitude similarity, using a +/−15% margin to determine similarity. If the data point, j, is sufficiently similar to the average of either the QRS or NOISE bin, it is then moved to that bin. Steps that move j to the QRS bin are shown at 338, 340, and steps that move j to the NOISE bin are shown at 342, 344.

After each data point in the EQUAL, HIGH and LOW bins has been considered in block 336, it is again determined whether there are 6 or more detections in the QRS bin, as indicated at 346. Next, the Averages for the NOISE and QRS bins are recalculated, as indicated at 350, for example, by the method of one of blocks 306 or 312 in FIG. 9A. Next, the SNR is determined as shown at 352, and a score is calculated as shown at 354. Once the Score is found at 354, the scoring method ends, as noted at 356.

If the condition at 346 fails, and there are still less than 6 detections in the QRS bin after block 338, the QRS, NOISE, HIGH, EQUAL and LOW bins may be reset to their original status prior to steps 336-344, as shown at 348. The method then goes to block Y 326, and continues in FIG. 9C.

Turning to FIG. 9C, the method continues from block Y 326. It is determined whether there are 2 or more detections in the HIGH bin, as indicated at 360. If not, then a bad vector is declared, as indicated at 362, and the scoring method ends because a score cannot be returned for the vector under consideration.

If there are at least 2 detections in the HIGH bin, the method goes from block 360 to 364, where the average amplitudes for the data points in the HIGH and LOW bins are computed. This may be performed using a method similar to those shown in one of blocks 306 or 312 in FIG. 9A or, instead, because the data set under consideration is already limited, the full set of data points in each bin may be used to calculate averages in step 364.

The next step is to attempt to move points from the EQUAL bin into the HIGH and LOW bins, as shown at 366. This is performed as indicated in block 368. For each data point k in the EQUAL bin, the amplitude stored for that data point is compared to the average for the HIGH bin, as shown at 370, to determine if it is similar to the average for the high bin, within a defined margin of +/−15%. If so, then the data point k is moved to the HIGH bin, as shown at 372. Otherwise, the amplitude for k is compared to the average for the LOW bin, again with a margin of +/−15%, as shown at 374. If the amplitudes are similar, k is moved to the LOW bin, as indicated at 376. These steps are repeated for each point k in the EQUAL bin.

After block 368 is completed, the method determines whether 4 or more detections are in the HIGH bin, as indicated at 380. If not, then a bad vector is declared as shown at 382, because no score can be returned. If there are 4 or more points in the HIGH bin, then possible scores are determined, as indicated by 384.

As shown in block 386, a TWave_Larger Score is calculated. This Possible Score assumes that the T-wave will have a greater amplitude than the QRS signal. Therefore, it assumes that the detections in the HIGH bin represent T-waves, while the detections in the LOW bin represent QRS signals. Therefore the SNR is calculated as the ratio of the average amplitude in the LOW bin to the average amplitude for the HIGH bin. This may be performed using the full data sets in each of the LOW bin and HIGH bin, or the data sets may be reduced by methods such as shown in blocks 306 and 312 in FIG. 9A. The variable "Amplitude" is then set as the average amplitude for the LOW bin (again, a full or reduced data set may be used to calculate the average amplitude for the LOW bin) as well. The Possible Score is determined as before by the use of the look-up table or chart, although again, other methods could also be used.

Next, as shown at 388, a QRS_Larger Score is calculated. This Possible Score assumes that the QRS signal will have a greater amplitude than the T-wave. Therefore, it assumes that the detections in the HIGH bin represent QRS signals, and the detections in the LOW bin represent T-waves. The SNR is calculated as the ratio of the average amplitude in the HIGH bin to the average amplitude in the LOW bin in similar fashion to that used in block 386, and the amplitude is calculated as the average amplitude for the HIGH bin, again using either full or reduced data sets. The Possible Score is then calculated as before.

After the creation of the Possible Scores (QRS_Larger SCORE and TWave_Larger Score) in steps 386, 388, a flag is set for asking the operator whether "QRS>TWave?" as indicated at 390. If necessary, i.e. if the largest available score is one of the possible scores, the operator can then provide an input that indicates which of the possible scores is correct. With the flag set at 390, the Scoring method ends as indicated at 392 by returning the two possible scores with the flag set.

Figure 10A:
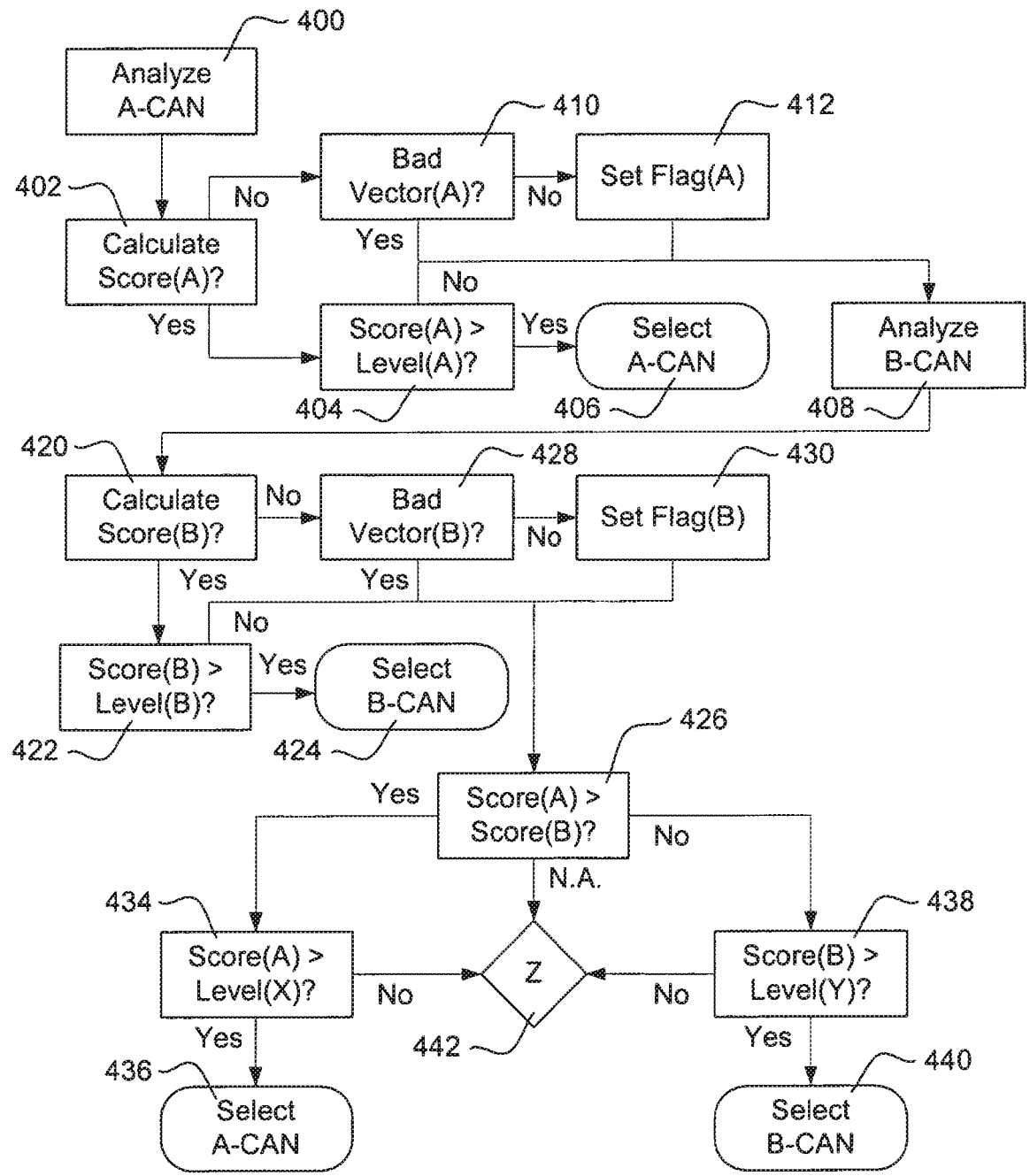
FIGS. 10A-10B illustrate a block diagram for a method of signal vector analysis.
Figure 10B:
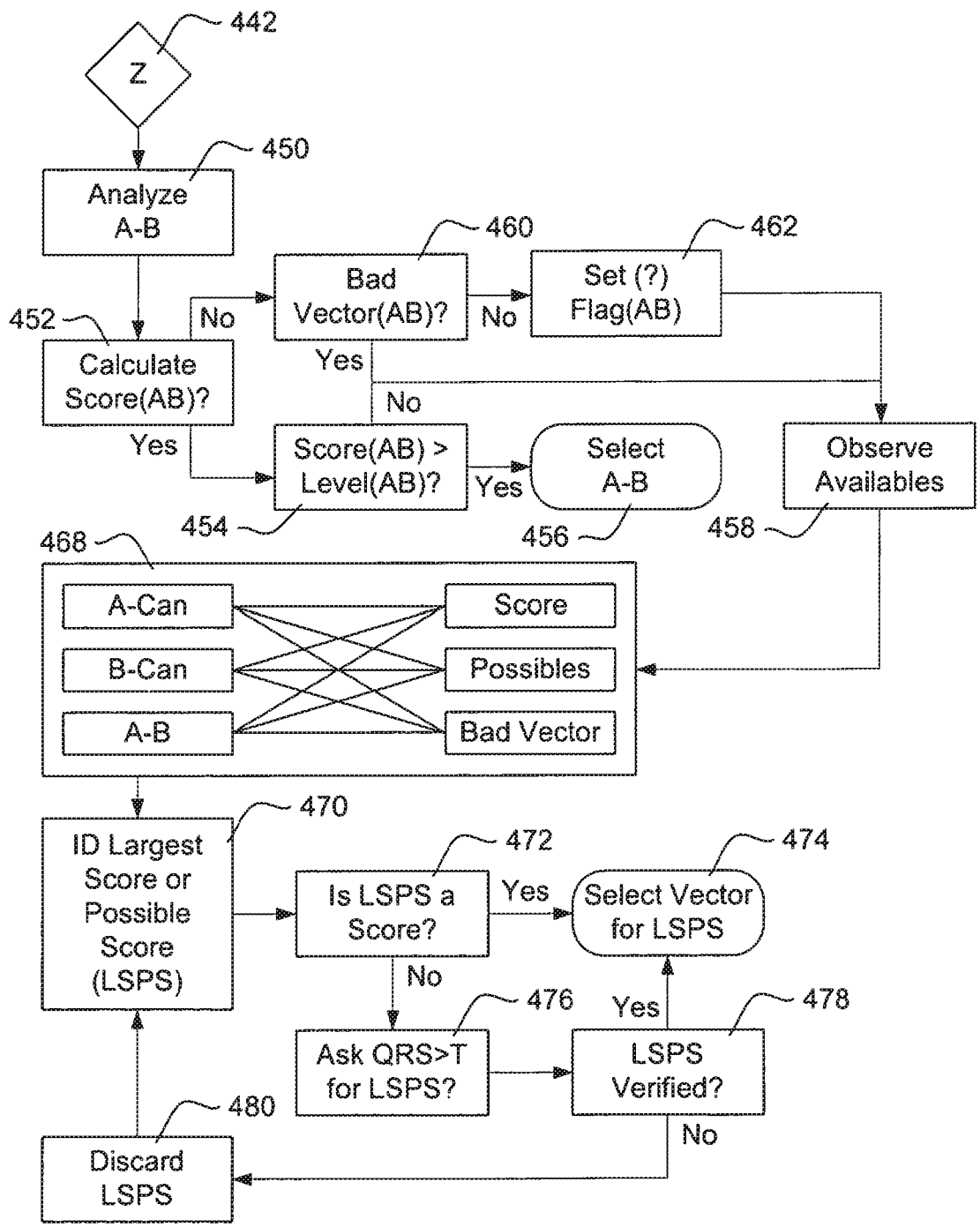

FIGS. 10A-10B illustrate a block diagram for a method of signal vector analysis. The method assumes a system as illustrated in one of FIGS. 1A-1B, with three sensing vectors available: A-Can, B-Can, and A-B. The illustrative vectoring method of FIGS. 10A-10B displays a preference for the A-Can vector, then the B-Can vector, and a lowest preference for the A-B vector. This is not necessary to the practice of the invention, but FIGS. 10A-10B illustrate how such preferences can be incorporated into a vectoring method.

The method begins at block 400, where the sensing vector A-Can is analyzed. As shown at 402, the first query is whether a Score(A) (a Score for the A-can sensing vector) has been calculated during the analysis 400. If so, the method continues at 404 where the generated Score(A) is compared to Level(A), a threshold for the A-Can sensing vector. If Score(A) exceeds Level(A), then the method selects the A-Can sensing vector, as indicated at 406, which ends the vectoring method if only one sensing vector is sought. If multiple sensing vectors are sought, then the method may continue by analyzing the other available vectors to select a secondary vector, if desired.

If Score(A) does not exceed Level(A), then the method goes to block 408, where the B-Can sensing vector is analyzed. Going back to block 402, if a Score cannot be calculated for the A-Can sensing vector, it is determined at 410 whether the A-Can sensing vector is a bad vector, as indicated at 410. If so, the A-Can sensing vector may be marked as bad, and the method jumps ahead to step 408. Otherwise, the method continues to block 412, where the flag for indicating that operator input is needed relative to the A-Can sensing vector is set. With analysis of the A-Can sensing vector complete, the method continues to block 408 where the B-can sensing vector is analyzed.

From block 408, it is again determined whether a Score (B) (a Score for the B-Can sensing vector) has been calculated, as shown at 420. If so, the method determines whether the Score(B) is greater than Level(B), a threshold for the B-Can sensing vector, as shown at 422. As before, if Level(B) is exceeded, the B-Can sensing vector is determined to be sufficient for detection use and the method ends (if only one sensing vector is sought) by selecting the B-Can sensing vector, as indicated at 424. If Level(B) is not exceeded, the method continues to step 426, further explained below.

If no Score(B) is calculated, the method determines whether the B-Can sensing vector is a bad vector, as indicated at 428. If so, the B-Can sensing vector may be marked as bad, and the method again continues at step 426. If the B-Can sensing vector is not a bad vector at 428, the method sets a flag indicating that operator input is needed to finish analysis of the B-Can vector to generate a Score, as indicated at 430. Again, the method continues to step 426.

At step 426, it is determined whether Score(A) exceeds Score(B). If a Score for either A-Can or B-Can could not be calculated, then step 426 will determine that whichever Score was calculated is greater. If neither Score was calculated, then the method goes directly to block Z 442 since the comparison is not applicable. If Score(A) is greater, then the method compares Score(A) to Level(X), a second threshold for the A-Can sensing vector, which may be lower than the threshold set by Level(A). If the second threshold is exceeded, the method selects A-Can, as shown at 436. Otherwise, the method goes to block Z 442. If Score(B) is greater, then the method compares Score(B) to Level(Y), a second threshold for the B-Can sensing vector, which may, again, be lower than the threshold set by Level(B). If Level(Y) is exceeded, the method selects the B-Can sensing vector, as indicated at 440. Otherwise, the method continues to block Z 442, which goes to FIG. 10B.

If desired, the thresholds Level(A) and Level(B) may be set at the same level. Likewise, the thresholds Level(X) and Level(Y) may also be set to the same level. In other embodiments, a factor may be included in the comparison at 426 to favor one or the other sensing vector. In another illustrative embodiment, the above look-up chart for finding factors SA and SR is used, with these factors next being multiplied to yield a Score. For the illustrative example, Level(A)=Level(B)=1750, and Level(X)=Level(Y)=750.

Referring now to FIG. 10B, the method continues from block Z 442 with the analysis of the A-B sensing vector, as indicated at 450. It is then determined whether a Score(AB) (the Score for sensing vector A-B) can be calculated, as indicated at 452. If so, then it is determined whether Score (AB) is greater than Level(AB), a threshold defined for the A-B sensing vector, as shown at 454. If so, then the A-B sensing vector is selected, as shown at 456. In an illustrative embodiment, Level(AB)=750, using the look-up chart to find SA and SR, and comparing the product of SA and SR to Level(AB). If Level(AB) is not exceeded, the method goes to step 458, which is further explained below.

If Score(AB) cannot be calculated at step 452, the method continues to step 460, where it is determined whether the A-B sensing vector is a bad vector. If so, the A-B sensing vector may be marked as a bad vector and the method continues to 458. If the A-B sensing vector is not a bad vector, the method continues to step 462 and sets the flag to indicate that operator input is needed to resolve an ambiguity with the A-B sensing vector. The method then continues to step 458, as explained below.

Step 458 indicates the observation of Available Scores. The Available Scores include calculated Scores and calculated Possible Scores. Block 468 indicates the characterizations that may occur. For each vector A-Can, B-Can, and A-B, there are three outcomes for the preceding illustrative example: a Score, a pair of Possible Scores, or a Bad Vector mark. As such there are 27 possible combinations, from 3 scores to 3 possible scores to 3 bad vectors, with a maximum of 6 Available Scores (2 Possible Scores for each sensing vector).

From the Available Scores, a largest score or possible score (LSPS) is identified, as shown at 470. Next, it is determined whether the LSPS is a Score, as indicated at 472. If so, then the sensing vector corresponding to the LSPS is selected, as shown at 474, and the method is over. If the LSPS is not a Score, then the operator is asked whether QRS>T for the sensing vector that corresponds to the LSPS, as indicated at 476. The answer given by the operator can either verify or reject the LSPS, depending upon whether the calculation resulting in the LSPS corresponds to the answer given by the operator.

For example, if the LSPS is the QRS_Larger Score for the A-Can sensing vector, the operator will be asked whether, for the A-Can sensing vector, QRS>Twave? If the operator indicates "Yes", then the operator's answer verifies the QRS_Larger Score for the A-Can sensing vector, and therefore the LSPS would be verified. If, instead, the operator's answer is No, then the TWave_Larger Score for the A-Can sensing vector would be verified, and the QRS_Larger Score would be discarded because the operator's answer indicates it is an incorrect calculation.

As indicated at 478, the method next determines whether the LSPS is verified by the operator's response to the question at 476. If so, then the sensing vector corresponding to the LSPS is selected, as indicated at 474. Otherwise, the LSPS is discarded, as indicated at 480, and the method returns to step 470, but this time with a Score for the LSPS sensing vector from the last iteration, rather than two Possible Scores.

Figure 11:
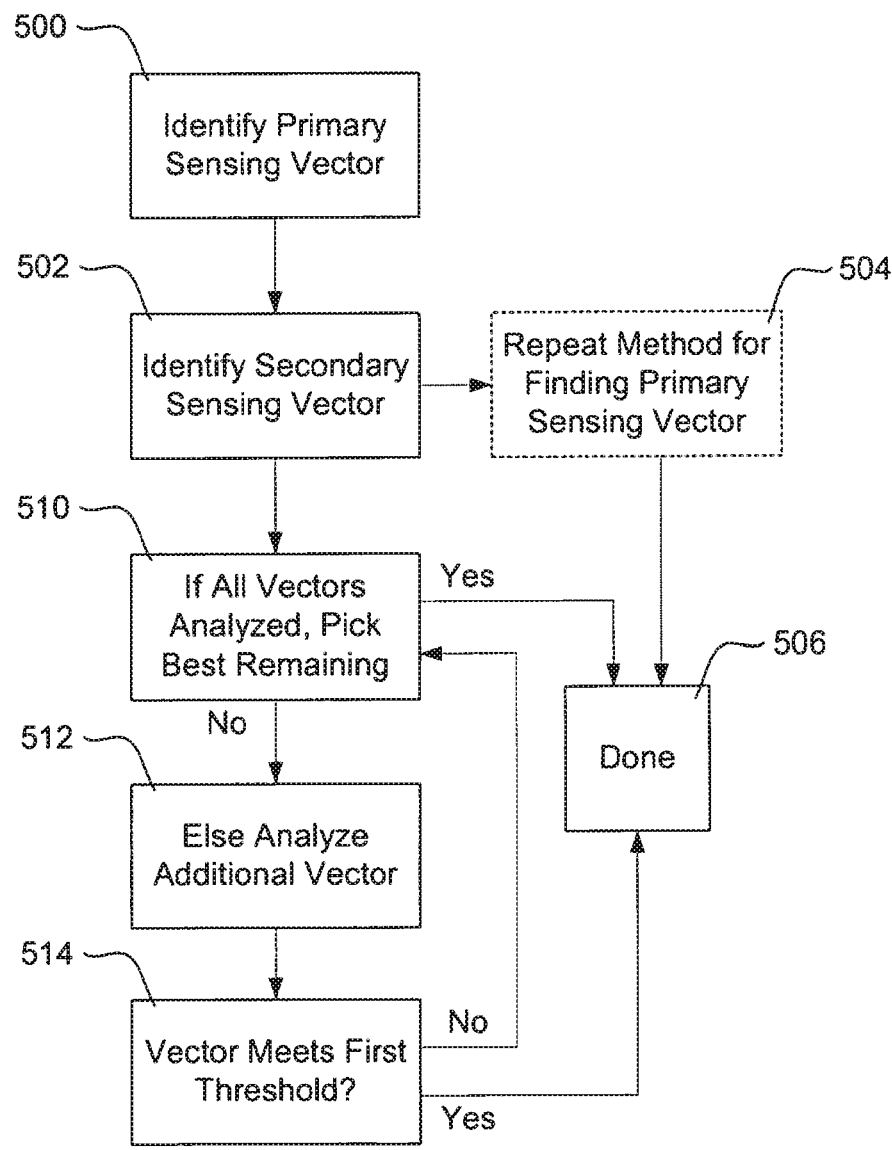
FIG. 11 is a block diagram illustrating a method in which a primary sensing vector and a secondary sensing vector are selected for use in detecting and analyzing cardiac events.

FIG. 11 is a block diagram illustrating a method in which a primary sensing vector and a secondary sensing vector are selected for use in detecting and analyzing cardiac events. As shown at 500, the method first identifies a primary sensing vector. This may be performed, for example, using the methods discussed above.

Next, the method includes identifying a secondary sensing vector, as shown at 502. This may be performed in more than one fashion. For example, as shown at 504, the method used to find the primary sensing vector may be repeated in its entirety, with the method ending at 506. In another embodiment, the method simply continues analysis after identifying the primary sensing vector. As shown at 510, if all of the available sensing vectors have already been analyzed, the method picks the best one and, again, ends at 506.

If not all vectors have been analyzed, then an additional vector is analyzed as shown at 512. If this additional vector meets a first threshold at step 514, illustrating that the additional vector is well suited to cardiac signal analysis, then the additional vector is selected as the secondary vector, and the method ends at 506. In another embodiment, a flag is set if not all vectors have been analyzed at 510, and an additional step is performed at the end of the method to compare the score for the primary vector to the score for the secondary vector. If the secondary vector has a higher score than the primary vector, their designations may be reversed.

If the additional vector does not meet the first threshold at step 514, the method loops back to step 510. The loop continues until either a newly analyzed vector exceeds the threshold at step 514, or all vectors have been analyzed and the best one is selected at step 510. The use of primary and secondary vectors may take several forms, such as those discussed in co-pending U.S. application Ser. No. 10/901, 258, filed Jul. 27, 2004, now U.S. Pat. No. 7,392,085 and titled MULTIPLE ELECTRODE VECTORS FOR IMPLANTABLE CARDIAC TREATMENT DEVICES, the disclosure of which is incorporated herein by reference.

Figure 12:
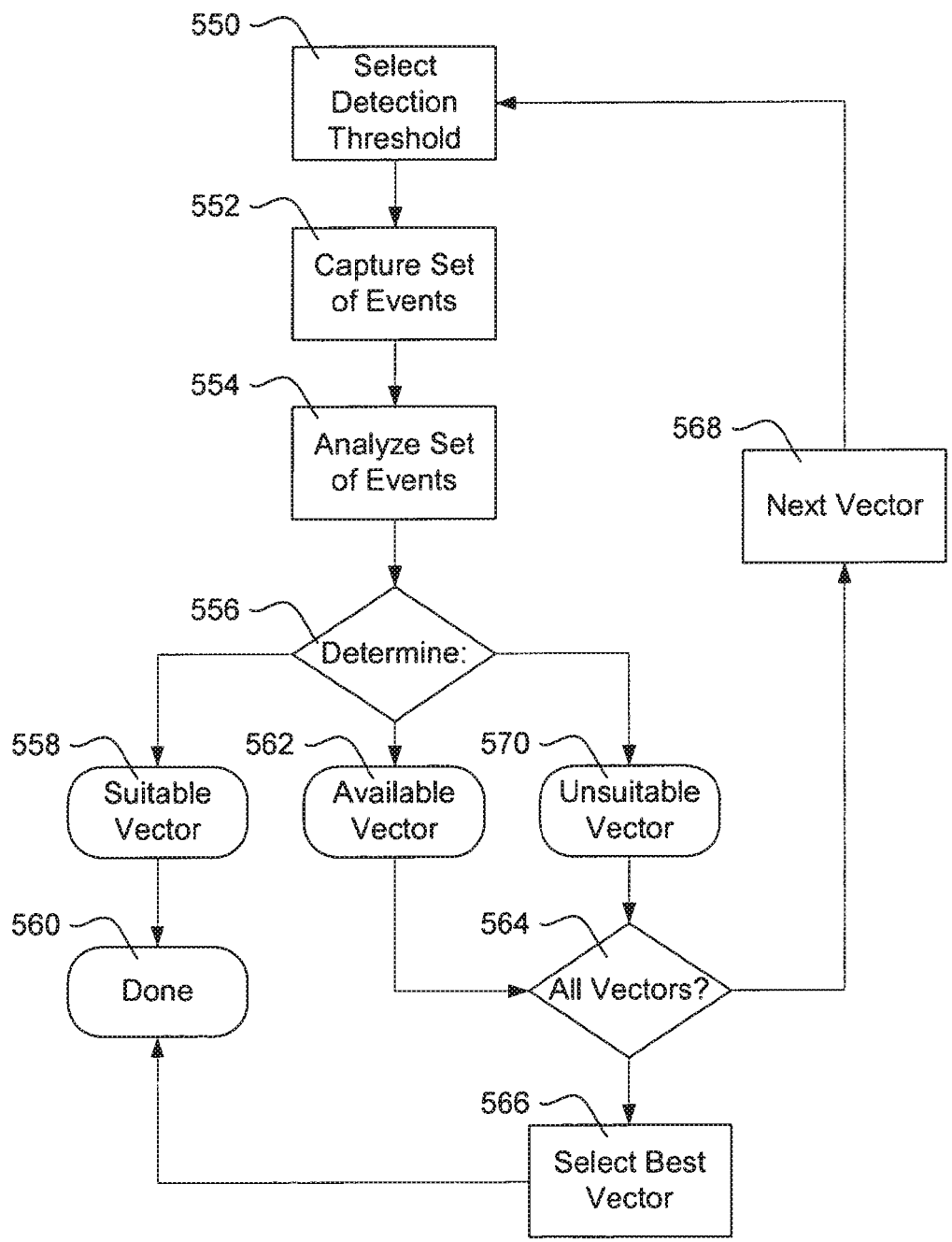
FIG. 12 is a block diagram for an illustrative embodiment.

FIG. 12 is a block diagram for an illustrative embodiment. The embodiment of FIG. 12 illustrates a generic method. Beginning at block 550, the method includes selecting a detection threshold. Next, a set of events is captured, as indicated at 552, using the detection threshold to define cardiac events sensed along a selected sensing vector. The set of events is analyzed as shown at 554. The analysis at 554 results in a determination at 556. The sensing vector used to capture the set of events at 552 is determined at step 556 to be one of a suitable vector, an available vector, or an unsuitable vector, as shown at 558, 562, and 570, respectively.

If the sensing vector is determined to be a suitable vector as shown at 558, then the sensing vector has been found to have met selected parameters for finding a suitable cardiac sensing vector. A vector meeting the selected parameters is, in the illustrative method, assumed to be likely sufficient to provide accurate cardiac monitoring. Therefore, in the illustrative method, further consideration of additional sensing vectors is considered unnecessary. Therefore, as indicated at 560, the method ends without further analysis of additional sensing vectors. The suitable vector is then used for cardiac event detection and analysis.

If, instead, the sensing vector is determined to be an available vector, as shown at 562, then the vector under consideration is considered a candidate for data capture, but does not meet the parameters to render further consideration of additional sensing vectors unnecessary. Also, an available vector 562 may be a sensing vector that indicates ambiguity in its analysis. The method then continues at 564, and determines whether all available sensing vectors have been analyzed. If so, the method continues to step 566, where the best vector is selected. Step 566 may include sub-methods to resolve ambiguities, if present, in the available or unsuitable vectors 562, 570. The method then ends at 560.

If not all sensing vectors have been considered when at step 564, the method continues by considering a different sensing vector, as indicated at 568. The method then returns to step 550 where a new detection threshold is selected for the "next" sensing vector.

Referring still to FIG. 12, in one illustrative example, a single sensing vector is available, due, for example, to limitations on the implanted device (i.e. only two electrodes are available) or due to a device failure (one or more electrodes may have a faulty connection). If, at step 566, a vector that has been determined to be unsuitable at 556 and 570 is selected, a flag may be set indicating that an error indicating poor sensing vector is to be annunciated to the programmer or, if the method is performed by the programmer itself, that the user or physician is to be notified.

The present invention includes certain embodiments in which the above methods may be performed by the implantable device in response to detected conditions, a request from an associated programmer, at intervals, or for other suitable reasons. Detected conditions prompting performance of vector analysis may include the occurrence of repeated difficulty with sensing, for example, the identification of an inordinate amount of double detections or a failure to consistently detect events. Another detected condition may be a rise in SNR or a drop in detected amplitude either below a predetermined level or to a level that creates sensing difficulties (for example, the range of 1.7 millivolts to 2.0 millivolts in a tiered sensor having 2.0 millivolt and 4.0 millivolt selectable dynamic sensing ranges).

These methods may be performed by an implantable cardiac stimulus device having a housing containing operational circuitry, or multiple housings tethered together containing operational circuitry distributed among the housings. The operational circuitry may be adapted to perform various of the above steps and methods using either or both of the analog and/or digital domain using appropriate components, devices, and connections, including but not limited to a microcontroller and associated memory.

In an illustrative embodiment in which one or more of the above methods are performed by an implantable medical device system, if it is determined that user input is needed to determine whether an identified LSPS corresponds to a score or a possible score, the method may include further steps. In particular, after the LSPS is identified, it may be determined whether a programmer is currently in communication with the implantable medical device system. If so, then telemetry circuitry/devices are used to contact the programmer to request the user input. Otherwise, the implantable medical device system sets aside the LSPS for later verification once a programmer is available for communication allowing the user input. If more than one LSPS is larger than the largest available Score, information indicating the successive next LSPS (or several LSPS's) may be stored until communication with a programmer is available.

Further, the present invention includes embodiments in which at least certain steps of the above methods may be performed by a programmer adapted for use with an implantable medical device, the programmer being adapted to communicate (for such embodiments, communication is preferably but not necessarily wireless) with an implantable medical device. The programmer may comprise various appropriate components and circuitry for performing method steps. The programmer may direct operation of the implantable medical device to perform the method(s), or the programmer may use the implantable medical device to capture data from the patient and transfer the captured data to the programmer itself. In some embodiments, certain method steps (event detection, for example) may be performed by the implantable medical device while other steps (detected event analysis, for example) may be performed by the associated programmer.

The present invention also includes embodiments in which machine readable media encodes an instruction set or sets for performing the above methods using operational circuitry of an implantable medical device or, in some embodiments, using circuitry in a programmer for use in association with an implantable medical device.

An illustrative embodiment includes a method involving an implantable medical system adapted to define a plurality of sensing vectors between electrodes implanted in a patient, and a programmer adapted for communication with the implantable medical device. The method may comprise the implantable medical system capturing cardiac signal data using at least one of the plurality of sensing vectors. Further, the method may include analyzing data related to the captured cardiac signal data and either determining that an identified sensing vector is suitable for cardiac event detection; or determining that one or more sensing vectors is to be analyzed.

The method may, if it is determined that one or more sensing vectors is to be analyzed, further comprise the implantable medical system capturing additional cardiac signal data using one or more other sensing vectors. Then, the method may also include analyzing data related to the captured additional cardiac signal data and: determining that an identified sensing vector is suitable for cardiac event detection; determining that there is a best available sensing vector; or using the programmer to request operator input to complete a sensing vector selection process.

In an illustrative embodiment of the above method, the analyzing and determining steps are performed by the programmer, and the method also comprises the implantable medical system transmitting data to the programmer for performing the analyzing and determining steps. Alternatively, the analyzing and determining steps are performed by the implantable medical system. If this is the case, the method may be such that the implantable medical system performs the capturing, analyzing and determining steps periodically and/or occasionally. In another embodiment, the implantable medical system performs the capturing, analyzing and determining steps in response to a request from the programmer. In some embodiments, the implantable medical system includes signal processing circuitry having at least a first dynamic range and a second dynamic range and, if the identified sensing vector is suitable for cardiac event detection, a dynamic range is selected.

Another illustrative embodiment includes a programmer for use with an implantable medical device system, the implantable medical device system including electrodes for sensing cardiac signals, the programmer comprising telemetry circuitry for communicating with the implantable medical device system, a user interface for communicating with an operator, and operational circuitry configured to perform a method of selecting a sensing vector for the implantable medical device system. The method of selecting a sensing vector may comprise a) directing the implantable medical device system to capture and transmit data related to a selected sensing vector; b) analyzing the transmitted data to determine if the selected sensing vector is well-suited for cardiac event detection; if the selected sensing vector is well suited for cardiac event detection, directing the implantable medical device system to use the selected sensing vector for cardiac event detection; or repeating steps a) and b) with another sensing vector.

The programmer may be such that the operational circuitry is further configured to perform the steps of, if a second sensing vector is well suited for cardiac event detection, directing the implantable medical device system to use the second sensing vector for cardiac event detection; or repeating steps a) and b) with a yet another sensing vector; if a third sensing vector is well suited for cardiac event detection, directing the implantable medical device system to use the third sensing vector for cardiac event detection; or x) identifying the best of the sensing vectors and directing the implantable medical device system to use the best sensing vector for cardiac event detection. The operational circuitry may be further configured to perform the steps of identifying an appropriate dynamic range for the implantable medical device system and directing the implantable medical device system to use the identified dynamic range. The operational circuitry may be adapted such that steps a) and b) allow for determination of at least an actual score or multiple possible scores, the multiple possible scores being determined when analysis reveals a likely ambiguity, each possible score corresponding to an outcome of the ambiguity. Step x) may include identifying a set of available scores including any scores and possible scores determined when steps b) were performed, y) selecting a best available score from the set of available scores; and, if the best available score is an actual score, identifying a corresponding sensing vector as the best of the sensing vectors, if the best available score is a possible score, requesting user input to eliminate the likely ambiguity, determining whether the user input verifies an outcome corresponding to the possible score and, if so, identifying a corresponding sensing vector as the best of the sensing vectors, or, if not, removing the possible score from the set of available scores and returning to step y).

In another embodiment, the operational circuitry is adapted such that steps a) and b) also allow for a determination that a vector is unsuitable for cardiac event detection, and, if a particular vector is determined to be unsuitable for cardiac event detection, that vector is not considered in step x). The operational circuitry may be adapted such that steps a) and b) include calculating either a score or, if ambiguity is likely, multiple possible scores for the selected sensing vector and the selected sensing vector is well-suited for cardiac event detection if a score is calculated and the score exceeds a threshold for the selected sensing vector. The operational circuitry may be adapted such that, if step b) is repeated for multiple sensing vectors, the threshold is adapted to each of the sensing vectors. The operational circuitry may comprise readable memory encoding an instruction set for performing the method of selecting a sensing vector.

An illustrative embodiment includes an implantable medical device system including electrodes for sensing cardiac signals and operational circuitry coupled to the electrodes, the electrodes defining a plurality of sensing vectors for observing electrical activity of a patient's heart, the operational circuitry configured to perform a method of selecting a sensing vector for the implantable medical device system. The method may comprise a) capturing data related to a selected sensing vector; b) analyzing the captured data to determine if the selected sensing vector is well-suited for cardiac event detection; if the selected sensing vector is well suited for cardiac event detection, using the selected sensing vector for cardiac event detection; or repeating steps a) and b) with another sensing vector. The operational circuitry may be further configured to perform the steps of, if the another sensing vector is well suited for cardiac event detection, using the second sensing vector for cardiac event detection; or repeating steps a) and b) with a yet another sensing vector; if the yet another sensing vector is well suited for cardiac event detection, using the yet another sensing vector for cardiac event detection; or x) identifying the best of the sensing vectors and using the best sensing vector for cardiac event detection. The implantable medical device system may further comprise telemetry circuitry for communicating with a programmer having a user interface, wherein the operational circuitry is adapted such that steps a) and b) allow for determination of at least an actual score or multiple possible scores, the multiple possible scores being determined when analysis reveals a likely ambiguity, each possible score corresponding to an outcome of the ambiguity; and step x) includes: identifying a set of available scores including any scores and possible scores determined when steps a) and b) were performed; y) selecting a best available score from the set of available scores and: if the best available score is an actual score, identifying a corresponding sensing vector as the best of the sensing vectors; if the best available score is a possible score, using the telemetry circuitry to direct the programmer to request user input to eliminate the likely ambiguity, receiving a response from the programmer indicating the user input, determining whether the user input verifies an outcome corresponding to the possible score and, if so, identifying a corresponding sensing vector as the best of the sensing vectors, or, if not, removing the possible score from the set of available scores and returning to step y).

The operational circuitry may be adapted such that steps a) and b) also allow for a determination that a vector is unsuitable for cardiac event detection, and, if a particular vector is determined to be unsuitable for cardiac event detection, that vector is not considered in step x). In another embodiment, the operational circuitry is adapted such that step b) includes calculating either a score or, if ambiguity is likely, multiple possible scores for the selected sensing vector and the selected sensing vector is well-suited for cardiac event detection if a score is calculated and the score exceeds a threshold for the selected sensing vector. The operational circuitry may be adapted such that, if step b) is repeated for multiple sensing vectors, the threshold is adapted to each of the sensing vectors. The operational circuitry may comprise readable memory encoding an instruction set for performing the method of selecting a sensing vector.

Another illustrative embodiment includes a method of cardiac signal analysis in an implantable cardiac stimulus system having at least first and second sensing electrodes defining a first sensing vector therebetween. The method may comprise selecting a detection threshold, capturing a plurality of detected events in which an electrical signal sensed along the first sensing vector exceeds the detection threshold, analyzing at least one metric related to a signal to noise ratio and amplitude for the plurality of detected events, determining whether the first sensing vector is suitable for cardiac event detection, unsuitable for cardiac event detection, or available for cardiac event detection.

Another illustrative embodiment is a method of directing operation of an implantable cardiac stimulus system comprising an implantable device having operational circuitry coupled to a plurality of sensing electrodes disposed within a patient and defining a plurality of sensing vectors for performing cardiac event detection, the system further comprising a programmer adapted for communication with the implantable device. The method may comprise the programmer directing data capture by the implantable device using at least one of the plurality of sensing vectors; and the programmer analyzing at least one of the plurality of sensing vectors and: determining that an identified sensing vector is suitable for cardiac event detection; or, determining that operator input is needed to complete a sensing vector selection process. The step of determining that operator input is needed to complete a sensing vector selection process may be used when ambiguity arises in the analyzing step. The operator input may be an indication of whether a T-wave component or a QRS-complex component of a cardiac signal, each captured using the same sensing vector, has a greater amplitude. The operator input may be an indication of whether a desired cardiac component of cardiac signal or a noise artifact, each using captured the same sensing vector, has a greater amplitude. The method may further include, if none of a set of at least two sensing vectors is determined to be suitable for cardiac event detection, the method includes requesting operator input using the programmer.

In another embodiment, the step of analyzing at least one of a plurality of the sensing vectors includes calculating a score related to the quality of detection available for a sensing vector, and the step of determining that an identified sensing vector is suitable for cardiac event detection includes comparing the score for the selected sensing vector to a threshold. The method may be such that the step of analyzing at least one of a plurality of the sensing vectors includes calculating a score related to the quality of detection available for a sensing vector, and the step of determining that an identified sensing vector is suitable for cardiac event detection includes selecting the sensing vector having the highest score. The step of analyzing at least one of a plurality of the sensing vectors may include attempting to calculate a score related to the quality of detection available for at least two of the sensing vectors, failing to calculate the score for at least one sensing vector due to uncertainty, establishing possible outcomes for the score given possible resolutions of the uncertainty, and setting a flag for the at least one sensing vector for which the score was not calculated. The method may be performed such that the step of determining that an identified sensing vector is suitable for cardiac event detection includes determining that a calculated score exceeds a predetermined threshold and selecting a corresponding sensing vector, or determining that a calculated score exceeds all other scores and possible outcomes and selecting a corresponding sensing vector; and the step of determining that operator input is needed includes determining that a possible outcome exceeds all other possible outcomes and calculated scores.

In one embodiment, the programmer may direct the implantable device to capture data and perform one or more steps of amplifying, filtering, and/or digitizing the captured data. In another embodiment, the implantable device is adapted to capture detections by comparison of a signal sensed using a sensing vector to a threshold, the programmer directs the implantable device to capture a set of detections using a sensing vector, and the programmer directs the implantable device to send data related to the set of detections to the programmer for use in the step of analyzing at least one of the plurality of sensing vectors.

Another illustrative embodiment includes a method of directing operation of an implantable cardiac stimulus system comprising an implantable device having operational circuitry coupled to a plurality of sensing electrodes disposed within a patient and defining a plurality of sensing vectors for performing cardiac event detection, the system further comprising a programmer adapted for communication with the implantable device. The method may comprise the programmer directing the implantable device to capture first data using a first sensing vector, the programmer directing the implantable device to transmit second data related to the captured first data, the programmer analyzing the transmitted second data to determine whether the first sensing vector is suitable, within given threshold conditions, for use in cardiac event detection and analysis, and if so, selecting the first vector for use in cardiac event detection and analysis; otherwise, the programmer directing the implantable device to capture and transmit additional data using one or more additional sensing vectors. The step of the programmer directing the implantable device to capture and transmit additional data using one or more additional sensing vectors may includes the programmer directing the implantable device to capture third data using a second sensing vector, the programmer directing the implantable device to transmit fourth data related to the captured third data, the programmer analyzing the transmitted fourth data to determine whether the second sensing vector is suitable, within given threshold conditions, for use in cardiac event detection and analysis, and if so, selecting the second cardiac vector for use in cardiac event detection and analysis, otherwise, the programmer directing the implantable device to capture and transmit additional data using at least a third sensing vector.

The step of the programmer directing the implantable device to capture and transmit additional data using one or more additional sensing vectors may include the programmer directing the implantable device to capture fifth data using a third sensing vector, the programmer directing the implantable device to transmit sixth data related to the captured fifth data, the programmer analyzing the transmitted sixth data to determine whether the third sensing vector is suitable, within given threshold conditions, for use in cardiac event detection and analysis and, if so, selecting the third cardiac vector for use in cardiac event detection and analysis, otherwise, the programmer selecting a best vector from among the first, second, and third sensing vectors for use in cardiac event detection and analysis. The step of the programmer directing the implantable device to capture and transmit additional data using one or more additional sensing vectors may include the programmer directing the implantable device to capture third data using a second sensing vector the programmer directing the implantable device to transmit fourth data related to the captured third data, the programmer analyzing the transmitted fourth data to determine whether the second sensing vector is suitable, within given threshold conditions, for use in cardiac event detection and analysis, and if so, selecting the second cardiac vector for use in cardiac event detection and analysis, otherwise, the programmer selecting a best vector from among the first and second sensing vectors for use in cardiac event detection and analysis.

Another illustrative embodiment includes a method of operating an implantable cardiac stimulus system comprising an implantable device having operational circuitry coupled to a plurality of sensing electrodes disposed within a patient and defining a plurality of sensing vectors for performing cardiac event detection, the system further comprising a programmer adapted for communication with the implantable device. The method may comprise executing instructions with the programmer to analyze at least first and second sensing vectors defined between selected subsets of the plurality of sensing electrodes by instructing the implantable device to perform data capture and transmission related to the at least first and second sensing vectors, the instructions adapted to generate either a score related to characteristics of a signal sensed along a selected sensing vector, or at least two possible scores and an indication of uncertainty relative to the possible scores; and, if no indications of uncertainty are generated, selecting whichever sensing vector has a highest score for use in detecting cardiac events, or, if at least one indication of uncertainty is generated: if a score exceeds other scores and all possible scores, selecting a corresponding sensing vector for use in detecting cardiac events without resolving uncertainty related to at least one possible score that does not exceed the identified score; and if an identified possible score exceeds all scores and other possible scores, requesting input from an operator to settle the uncertainty related to the possible score and, if the operator input resolves the uncertainty in favor of the identified possible score, selecting a corresponding sensing vector for use in detecting cardiac events.

The step of requesting input from an operator may include asking the operator to determine whether the peak amplitude of a sensed QRS complex is greater than the peak amplitude of a sensed T-wave. Also, the step of requesting input from an operator may include asking the operator to determine whether the peak amplitude of a sensed QRS complex is greater than the peak amplitude of a sensed noise signal. Further, the step of requesting input from an operator includes asking the operator to determine whether a highest peak in a sensed signal is an R-wave peak.

Another illustrative embodiment includes a method of operating an implantable cardiac stimulus system comprising an implantable device having operational circuitry to coupled to a plurality of sensing electrodes disposed within a patient and defining a plurality of sensing vectors for performing cardiac event detection, the system further comprising a programmer adapted for communication with the implantable device. The method may comprise executing vectoring instructions with the programmer to analyze a first sensing vector defined between a selected subset of the plurality of sensing electrodes by at least instructing the implantable device to perform data capture and transmission related to the first sensing vector, wherein the vectoring instructions are adapted to generate either a score related to characteristics of a signal sensed along a selected sensing vector, or at least two possible scores and an indication of uncertainty relative to the possible scores; if the analysis of the first sensing vector generates a first score, comparing the first score to a first threshold and, if the first score exceeds the first threshold, selecting the first sensing vector for use in detecting cardiac events; otherwise, executing the vectoring instructions with the programmer to analyze a second sensing vector defined between another selected subset of the plurality of sensing electrodes by at least instructing the implantable device to perform data capture and transmission related to the second sensing vector; and if the analysis of the second sensing vector generates a second score, comparing the second score to a second threshold and, if the second score exceeds the second threshold, selecting the second sensing vector for use in detecting cardiac events.

The method may be such that the second sensing vector is not analyzed if the first score exceeds the first threshold. The method may further comprise, if the first score does not exceed the first threshold or a first score is not generated, and the second score does not exceed the second threshold or a second score is not generated; then, executing the vectoring instructions with the programmer to analyze a third sensing vector defined between yet another selected subset of the plurality of sensing electrodes by at least instructing the implantable device to perform data capture and transmission related to the third sensing vector; and if the analysis of the third sensing vector generates a third score, comparing the third score to a third threshold and, if the third score exceeds the third threshold, selecting the third sensing vector for use in detecting cardiac events.

In another method, if none of the first, second or third thresholds are exceeded, the method further comprises starting with a set of scores and/or possible scores generated by executing the vectoring instructions: a) identifying a greatest available score from the scores and/or possible scores; b) if the greatest available score is a score, selecting sensing vector corresponding to the score for use in detecting cardiac events; c) if a greatest available score is a possible score, requesting input from an operator to determine whether the identified possible score should be treated as an actual score or discarded; d) if the operator input indicates that the identified possible score should be treated as an actual score, selecting a sensing vector corresponding to the identified possible score for use in detecting cardiac events; e) if the operator input indicates that the identified possible score should be discarded, removing the identified possible score from the set of scores and/or possible scores, treating an associated possible score as a score, and returning to step a). The method may be such that, if first and second scores are generated by executing the vectoring instructions on the first and second sensing vectors and neither score exceeds a corresponding threshold, the method further comprises determining whether the greater of the first and second scores exceeds a third threshold and, if so, selecting the greater of the first and second scores for use in detecting cardiac events.

The scores and possible scores may be generated by calculating a signal-to-noise ratio and observing a peak amplitude for a selected sensing vector. The scores and possible scores may also be generated by inserting the signal-to-noise ratio and observed peak amplitude into a formula. Instead, the scores and possible scores may be generated by inserting the signal-to-noise ratio and observed peak amplitude into a look-up table.

Another illustrative embodiment includes a method of operating an implantable cardiac stimulus system comprising an implantable device having operational circuitry coupled to a plurality of sensing electrodes disposed within a patient and defining a plurality of sensing vectors for performing cardiac event detection, the system further comprising a programmer adapted for communication with the implantable device. The method may comprise the programmer instructing the implantable device to perform at least data capture and transmission relative to a first sensing vector, the programmer analyzing transmitted data related to the first sensing vector and returning one of: a) a score indicating the quality of a signal captured along the first sensing vector; b) at least two possible scores indicating the quality of the signal captured along the first sensing vector wherein operator input is needed to determine which possible score is correct; or c) an indication that the sensing vector under review is unsuitable for cardiac signal sensing; the programmer determining whether the first sensing vector receives a score indicating that the first sensing vector is well suited to cardiac signal detection and, if not, the programmer instructing the implantable device to perform at least data capture and transmission relative to a second sensing vector; and the programmer analyzing transmitted data related to the second sensing vector in similar fashion to the first sensing vector. The method may further comprise the programmer determining whether the second sensing vector receives a score indicating that the second sensing vector is well suited to cardiac signal detection and, if not, the programmer identifying which of the returned scores or possible scores is highest and, if a possible score is highest, the programmer querying an operator for the device to determine whether the highest possible score is correct; if so, a corresponding sensing vector is selected for use in detecting cardiac activity; else, the programmer repeats the step of selecting which of the returned scores or possible scores is highest until a sensing vector is selected.

Another illustrative embodiment includes a method of operating an implantable cardiac stimulus system comprising operational circuitry coupled to a plurality of sensing electrodes disposed within a patient and defining a plurality of sensing vectors for performing cardiac event detection. The method may comprise the operational circuitry analyzing at least one of the plurality of sensing vectors; and the operational circuitry either: determining that an identified sensing vector is suitable for cardiac event detection; or determining that operator input is needed to complete a sensing vector selection process. The step of determining that operator input is needed to complete a sensing vector selection process may be a step of last resort used when the operational circuitry cannot resolve or eliminate ambiguity in the analyzing step. The operator input may be an indication of whether a T-wave component or a QRS-complex component of a cardiac signal, each captured using the same sensing vector, has a greater amplitude. The operator input may be an indication of whether a desired cardiac component of cardiac signal or a noise artifact, each using captured the same sensing vector, has a greater amplitude.

The method may be such that the step of determining that operator input is needed is performed only after all of the sensing vectors have been analyzed. In another method, the step of analyzing at least one of a plurality of the sensing vectors includes calculating a score related to the quality of detection available for a sensing vector; and the step of determining that an identified sensing vector is suitable for cardiac event detection includes comparing the score for the selected sensing vector to a threshold. In yet another method, the step of analyzing at least one of a plurality of the sensing vectors includes calculating a score related to the quality of detection available for a sensing vector; and the step of determining that an identified sensing vector is suitable for cardiac event detection includes selecting the sensing vector having the highest score. The step of analyzing at least one of a plurality of the sensing vectors may include attempting to calculate a score related to the quality of detection available for at least two of the sensing vectors, failing to calculate the score for at least one sensing vector due to uncertainty, establishing possible outcomes for the score given possible resolutions of the uncertainty, and setting a flag for the at least one sensing vector for which the score was not calculated. The method may also be such that the step of determining that an identified sensing vector is suitable for cardiac event detection includes determining that a calculated score exceeds a predetermined threshold and selecting a corresponding sensing vector; or determining that a calculated score exceeds all other scores and possible outcomes and selecting a corresponding sensing vector; and the step of determining that operator input is needed includes determining that a possible outcome exceeds all other possible outcomes and calculated scores.

Another illustrative embodiment includes a method of operating an implantable cardiac stimulus system comprising operational circuitry coupled to a plurality of sensing electrodes disposed within a patient and defining a plurality of sensing vectors for performing cardiac event detection. The method may comprise analyzing a first sensing vector to determine whether it is suitable, within given threshold conditions, for use in cardiac event detection and analysis, and if so, selecting the first vector for use in cardiac event detection and analysis, otherwise, analyzing one or more additional sensing vectors. The step of analyzing one or more additional vectors may include analyzing a second sensing vector to determine whether it is suitable, within given threshold conditions, for use in cardiac event detection and analysis, and if so, selecting the second cardiac vector for use in cardiac event detection and analysis; and, otherwise, analyzing at least a third sensing vector.

The step of analyzing at least a third sensing vector may include determining whether the third sensing vector is suitable, within given threshold conditions, for use in cardiac event detection and analysis and, if so, selecting the third cardiac vector for use in cardiac event detection and analysis; and, otherwise, selecting a best vector from among the first, second, and third sensing vectors for use in cardiac event detection and analysis. The step of analyzing one or more additional vectors may include analyzing a second sensing vector to determine whether it is suitable, within given threshold conditions, for use in cardiac event detection and analysis; and, if so, selecting the second cardiac vector for use in cardiac event detection and analysis; else, selecting a best vector from among the first and second sensing vectors for use in cardiac event detection and analysis.

Another illustrative embodiment includes a method of operating an implantable cardiac stimulus system comprising a controller coupled to a plurality of sensing electrodes adapted for disposition in a patient. The method may comprise executing instructions with the controller to analyze at least first and second sensing vectors defined between selected subsets of the plurality of sensing electrodes, the instructions adapted to generate either a score related to characteristics of a signal sensed along a selected sensing vector, or at least two possible scores and an indication of uncertainty relative to the possible scores; and, if no indications of uncertainty are generated, selecting whichever sensing vector has a highest score for use in detecting cardiac events. If at least one indication of uncertainty is generated, and if a score exceeds other scores and all possible scores, the method may include selecting a corresponding sensing vector for use in detecting cardiac events without resolving uncertainty related to at least one possible score that does not exceed the identified score; or if an identified possible score exceeds all scores and other possible scores, the method may include requesting input from an operator to settle the uncertainty related to the possible score and, if the operator input resolves the uncertainty in favor of the identified possible score, selecting a corresponding sensing vector for use in detecting cardiac events.

The step of requesting input from an operator may include asking the operator to determine whether the peak amplitude of a sensed QRS complex is greater than the peak amplitude of a sensed T-wave. The step of requesting input from an operator may include asking the operator to determine whether the peak amplitude of a sensed QRS complex is greater than the peak amplitude of a sensed noise signal. The step of requesting input from an operator may include asking the operator to determine whether a highest peak in a sensed signal is an R-wave peak.

Another illustrative embodiment includes a method of operating an implantable cardiac stimulus system comprising a controller coupled to a plurality of sensing electrodes adapted for disposition in a patient. The method may comprise executing vectoring instructions with the controller to analyze a first sensing vector defined between a selected subset of the plurality of sensing electrodes, wherein the vectoring instructions are adapted to generate either a score related to characteristics of a signal sensed along a selected sensing vector, or at least two possible scores and an indication of uncertainty relative to the possible scores; if the analysis of the first sensing vector generates a first score, comparing the first score to a first threshold and, if the first score exceeds the first threshold, selecting the first sensing vector for use in detecting cardiac events; otherwise, executing the vectoring instructions with the controller to analyze a second sensing vector defined between another selected subset of the plurality of sensing electrodes; and if the analysis of the second sensing vector generates a second score, comparing the second score to a second threshold and, if the second score exceeds the second threshold, selecting the second sensing vector for use in detecting cardiac events. The method may be such that the second sensing vector is not analyzed if the first score exceeds the first threshold.

If the first score does not exceed the first threshold or a first score is not generated, and the second score does not exceed the second threshold or a second score is not generated, then the method may also include executing the vectoring instructions with the controller to analyze a third sensing vector defined between yet another selected subset of the plurality of sensing electrodes, and if the analysis of the third sensing vector generates a third score, comparing the third score to a third threshold and, if the third score exceeds the third threshold, selecting the third sensing vector for use in detecting cardiac events. If none of the first, second or third thresholds are exceeded, the method may further comprise starting with a set of scores and/or possible scores generated by executing the vectoring instructions and: a) identifying a greatest available score from the scores and/or possible scores; b) if the greatest available score is a score, selecting sensing vector corresponding to the score for use in detecting cardiac events; c) if a greatest available score is a possible score, requesting input from an operator to determine whether the identified possible score should be treated as an actual score or discarded; d) if the operator input indicates that the identified possible score should be treated as an actual score, selecting a sensing vector corresponding to the identified possible score for use in detecting cardiac events; e) if the operator input indicates that the identified possible score should be discarded, removing the identified possible score from the set of scores and/or possible scores, treating an associated possible score as a score, and returning to step a).

If first and second scores are generated by executing the vectoring instructions on the first and second sensing vectors and neither score exceeds a corresponding threshold, the method may include determining whether the greater of the first and second scores exceeds a third threshold and, if so, selecting the greater of the first and second scores for use in detecting cardiac events. The method may be such that the scores and possible scores are generated by calculating a signal-to-noise ratio and observing a peak amplitude for a selected sensing vector. Also, the scores and possible scores may be generated by inserting the signal-to-noise ratio and observed peak amplitude into a formula. The scores and possible scores may also be generated by inserting the signal-to-noise ratio and observed peak amplitude into a look-up table.

Another illustrative embodiment includes a method of cardiac signal analysis in an implantable cardiac stimulus system having a plurality of sensing electrodes and operational circuitry coupled thereto. The method may comprise the operational circuitry executing vectoring instructions relative to a first sensing vector, the vectoring instructions causing the operational circuitry to return one of: a) a score indicating the quality of a signal captured along the first sensing vector; b) at least two possible scores indicating the quality of the signal captured along the first sensing vector wherein operator input is needed to determine which possible score is correct; or c) an indication that the sensing vector under review is unsuitable for cardiac signal sensing. The method may also include the operational circuitry determining whether the first sensing vector receives a score indicating that the first sensing vector is well suited to cardiac signal detection and, if not, the operational circuitry executing the vectoring instructions relative to a second sensing vector. The method may further comprise the operational circuitry determining whether the second sensing vector receives a score indicating that the second sensing vector is well suited to cardiac signal detection and, if not, the operational circuitry selecting which of the returned scores or possible scores is highest and, if a possible score is highest, the operational circuitry querying an operator for the device to determine whether the highest possible score is correct; if so, a corresponding sensing vector is selected for use in detecting cardiac activity; else, the operational circuitry repeats the step of selecting which of the returned scores or possible scores is highest until a sensing vector is selected.

An illustrative embodiment includes a method of cardiac signal analysis comprising analyzing data captured along one or more of a plurality of sensing vectors defined between implanted electrodes and selecting one of the plurality of sensing vectors for primary use in cardiac event detection. The step of analyzing data captured along one of the plurality of sensing vectors may include identifying a number of detected events by comparison of a received signal to a detection threshold, characterizing, by analysis of intervals between the detected events, the detected events as: a) QRS events; b) artifacts; or c) unidentifiable; and, if sufficient detected events are QRS events, calculating a signal-to-noise ratio and amplitude associated with the sensing vector; otherwise parsing, by analysis of event intervals and amplitudes, the unidentifiable events into: a) QRS events; b) artifacts; or c) unparseable. At this point, if sufficient detected events are now QRS events, the method includes calculating a signal-to-noise ratio and amplitude associated with the sensing vector. The method may be performed by operational circuitry of an implanted medical device. The step of identifying a number of detected events may be performed by an implantable medical device, and the other steps are performed by a programmer adapted to communicate with the implantable medical device. In yet another method, at least one step is performed by an implantable medical device and at least one other step is performed by a programmer adapted to communicate with the implantable medical device.

Devices, including implantable medical devices and programmers, that are adapted to perform one or more steps of the above methods, as well as systems comprising implantable medical devices and programmers that are adapted as systems to perform any of these methods and/or steps, are also included in illustrative embodiments.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A medical device comprising an implantable stimulus device including an implantable lead and operational circuitry contained within a housing, the operational circuitry coupled to a plurality of electrodes for sensing cardiac activity, wherein the plurality of electrodes includes at least one electrode on the housing and at least one electrode on the lead; the operational circuitry being configured to perform the following:
   receive a signal from the electrodes;
   sense a plurality of detected events from the signal received from the electrodes, the detected events separated by intervals;
   analyze consecutive intervals defined between pairs of detected events;
   determine that at least two consecutive intervals are equal within a predefined margin;
   determine that each of the at least two equal consecutive intervals are shorter than a predefined duration; and
   after determining the consecutive intervals are equal within the predefined margin and shorter than the predefined duration, mark whichever of the two detected events occurring at the start of each of the consecutive intervals is of lesser amplitude as noise and the other of the two detected events as QRS; and
   wherein the operational circuitry is configured to sense the plurality of detected events by:
   comparing a sensing threshold set to a selected amplitude to the received signal from the electrodes;
   observing crossing of the sensing threshold and declaring a detected event;
   applying a refractory period for predetermined period of time; and
   again comparing the sensing threshold set to the selected amplitude to the received signal from the electrodes after the refractory period to sense a subsequent detected event.

2. The medical device of claim 1 wherein the plurality of electrodes define a plurality of sensing vectors and the operational circuitry is configured to perform vector selection to select a default vector for use in sensing cardiac activity, in which the operational circuitry is configured to analyze said detected events marked as QRS to determine an amplitude factor used for vector selection.

3. The medical device of claim 2 wherein the operational circuitry is configured to analyze said detected events marked as noise to determine a noise factor used for vector selection.

4. The medical device of claim 1 wherein the plurality of electrodes define a plurality of sensing vectors and the operational circuitry is configured to perform vector selection to select a default vector for use in sensing cardiac activity, in which the operational circuitry is configured to analyze detected events marked as noise to determine a noise factor used for vector selection.

5. The medical device of claim 1 wherein the operational circuitry is configured to set the selected amplitude in a setting process by:
   the operational circuitry setting an initial sensing floor;
   the operational circuitry comparing the initial sensing floor to the received signal until the received signal crosses the initial sensing floor;
   the operational circuitry raising the sensing floor until a timeout occurs; and
   the operational circuitry setting the selected amplitude relative a level of the sensing floor at which the timeout occurs.

6. A medical device as in claim 1 wherein the implantable cardiac stimulus device is configured as a subcutaneous-only implantable defibrillator such that all electrodes are disposed outside of the ribcage of the patient.

7. A medical device as in claim 1 wherein the implantable cardiac stimulus device is configured as a transvenous implantable defibrillator such that the lead is configured to enter the patient's venous system and attach to the heart thereof.

8. A medical device as in claim 1 wherein the housing has at least two electrodes disposed thereon.

9. A medical device as in claim 1, wherein the operational circuitry is configured such that the predefined margin calls for the duration of the at least two consecutive intervals to be within a set time period of one another.

10. A medical device as in claim 9 wherein the set time period is 50 milliseconds.

11. A method of operation in a medical device comprising a housing, an implantable lead, a plurality of electrodes and operational circuitry disposed within the housing, the operational circuitry coupled to the plurality of electrodes for sensing cardiac activity, the plurality of electrodes includes at least one electrode on the housing and at least one electrode on the lead, the method comprising the operational circuitry:
   receiving a signal from the electrodes;
   sensing a plurality of detected events from the signal received from the electrodes, the detected events separated by intervals;
   analyzing consecutive intervals defined between pairs of detected events;
   determining that at least two consecutive intervals are equal, within a predefined margin;
   determining that the at least two equal consecutive intervals are each shorter than a predefined duration;
   after determining the consecutive intervals are equal within the predefined margin and shorter than the predefined duration, marking whichever of the two detected events occurring at the start of each of the consecutive intervals is of lesser amplitude as noise and the other of the two detected events as QRS; and
   using the QRS to identify and select a default sensing vector for the medical device and using the default sensing vector to sense cardiac activity of a patient;

wherein the operational circuitry is configured to sense the plurality of detected events by:
  comparing a sensing threshold set to a selected amplitude to the received signal from the electrodes;
  observing crossing of the sensing threshold and declaring a detected event;
  applying a refractory period for predetermined period of time; and
  again comparing the sensing threshold set to the selected amplitude to the received signal from the electrodes after the refractory period to sense a subsequent detected event.

12. A method of vector selection in a medical device having a plurality of electrodes that define a plurality of sensing vectors and operational circuitry coupled to the plurality of electrodes, the method comprising:
  performing the method of claim 11; and
  analyzing said detected events marked as QRS to determine an amplitude factor used for vector selection.

13. A method of vector selection as in claim 12, further comprising analyzing said detected events marked as noise to determine a noise factor used for vector selection.

14. A method of vector selection in a medical device having a plurality of electrodes that define a plurality of sensing vectors and operational circuitry coupled to the plurality of electrodes, the method comprising:
  performing the method of claim 11; and
  analyzing detected events marked as noise to determine a noise factor used for vector selection.

15. A method as in claim 11 further comprising the operational circuitry setting the selected amplitude by:
  setting an initial sensing floor;
  comparing the initial sensing floor to the received signal until the received signal crosses the initial sensing floor;
  raising the sensing floor until a timeout occurs; and
  setting the selected amplitude relative to a level of the sensing floor at which the timeout occurs.

16. A method as in claim 11 wherein the medical device is a subcutaneous-only implantable defibrillator, and the operational circuitry comprises a charging sub-circuit and a power storage sub-circuit for building up a stored voltage for cardiac stimulus taking the form of defibrillation therapy, and the method further comprises the operational circuitry using the selected sensing vector to identify a treatable arrhythmia and the operational circuitry delivering a defibrillation therapy, and the step of receiving a signal from the electrodes is performed using electrodes placed outside of the ribcage of a patient.

17. A method as in claim 11 wherein the medical device is a transvenous defibrillator and the implantable lead is configured to be placed inside of the heart of a patient, and the operational circuitry comprises a charging sub-circuit and a power storage sub-circuit for building up a stored voltage for cardiac stimulus taking the form of defibrillation therapy, and the method further comprises the operational circuitry using the selected sensing vector to identify a treatable arrhythmia and the operational circuitry delivering a defibrillation therapy, and the step of receiving a signal from the electrodes is performed using one or more electrodes in or on the heart.

18. A method as in claim 11 wherein the housing has at least two electrodes disposed thereon.

19. A method as in claim 11, wherein the operational circuitry is configured such that the predefined margin calls for the durations of the at least two consecutive intervals to be within a set time period of one another.

20. A method as in claim 19 wherein the set time period is 50 milliseconds.

* * * * *